(12) United States Patent
Carell

(10) Patent No.: US 11,370,756 B2
(45) Date of Patent: Jun. 28, 2022

(54) SULFOXIDE-BASED REAGENT FOR MASS SPECTROMETRY

(71) Applicant: Roche Diagnostics Operations, Inc., Indianapolis, IN (US)

(72) Inventor: Thomas Carell, Krailing (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 292 days.

(21) Appl. No.: 16/811,298

(22) Filed: Mar. 6, 2020

(65) Prior Publication Data

US 2020/0199071 A1 Jun. 25, 2020

Related U.S. Application Data

(63) Continuation of application No. PCT/EP2018/073812, filed on Sep. 5, 2018.

(30) Foreign Application Priority Data

Sep. 8, 2017 (EP) .................................. 17190147

(51) Int. Cl.
C07D 207/46 (2006.01)
G01N 33/58 (2006.01)
G01N 33/68 (2006.01)

(52) U.S. Cl.
CPC ........... *C07D 207/46* (2013.01); *G01N 33/58* (2013.01); *G01N 33/6848* (2013.01)

(58) Field of Classification Search
None
See application file for complete search history.

(56) References Cited

U.S. PATENT DOCUMENTS

2017/0082635 A1 3/2017 Rychnovsky et al.

FOREIGN PATENT DOCUMENTS

GB 2156818 A 10/1985
GN 104672241 A 6/2015

OTHER PUBLICATIONS

Young et al., Inhibition of Inducible Nitric Oxide Synthase by Acetamidine Derivatives of Hetero-Substituted Lysine and Homolysine, Bioorganic & Medicinal Chemistry Letters 10 (2000) 597-600.
International Search Report dated Oct. 17, 2018, in Application No. PCT/EP2018/073812, 3 pp.
Stadlmeier, Michael et al., A Sulfoxide-Based Isobaric Labelling Reagent for Accurate Quantitative Mass Spectrometry, Angewandte Chemie International Edition, 2018, pp. 2958-2962, vol. 57, No. 11.
Thingholm, Tine E. et al., Undesirable Charge-Enhancement of Isobaric Tagged Phosphopeptides Leads to Reduced Identification Efficiency, Journal of Proteome Research, 2010, pp. 4045-4052, vol. 9, No. 8.

(Continued)

*Primary Examiner* — Xiaoyun R Xu
(74) *Attorney, Agent, or Firm* — Stinson LLP

(57) ABSTRACT

The present disclosure relates to sulfoxide-based reagents suitable in the mass spectrometric determination of analyte molecules such as peptides as well as adducts of such reagents and analyte molecules and applications of the reagents and adducts. Further, the present disclosure relates to methods for the mass spectrometric determination of analyte molecules.

16 Claims, 4 Drawing Sheets

(56) References Cited

OTHER PUBLICATIONS

Virreira Winter, Sebastian et al., EASI-tag enables accurate multiplexed and interface-free MS2-based proteome quantification. Nature Methods, 2018, pp. 527-530, vol. 15, No. 7.

Yu, Clinton et al., Developing a Multiplexed Quantitative Cross-Linking Mass Spectrometry Platform for Comparative Structural Analysis of Protein Complexes, Analytical Chemistry, 2016, pp. 10301-10308, vol. 88, No. 20.

Figure 2A
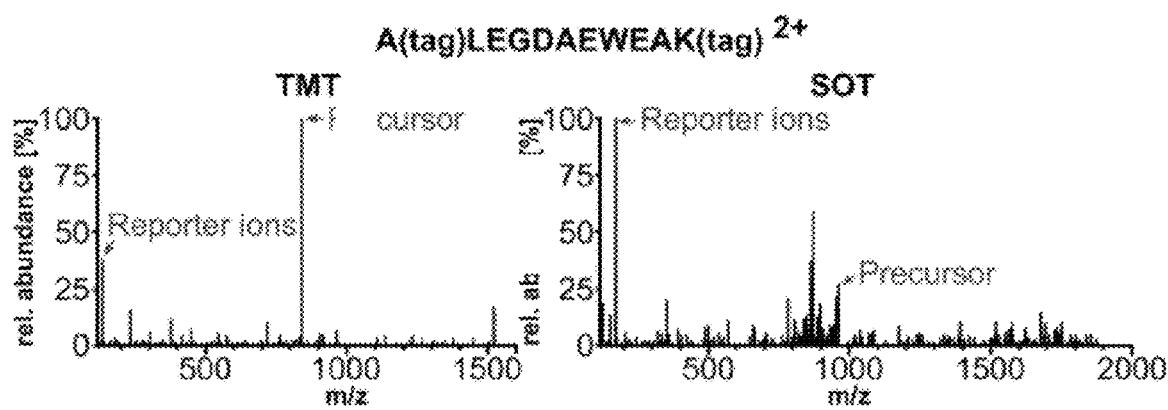
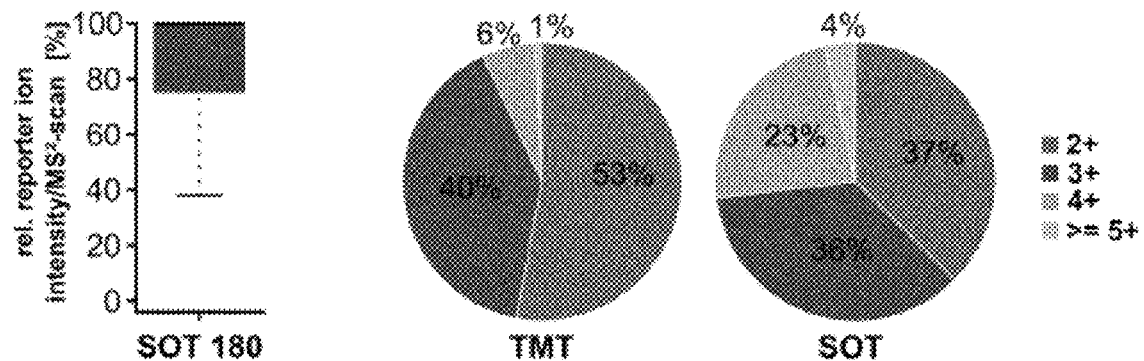
Figure 2B   Figure 2C

Figure 3A
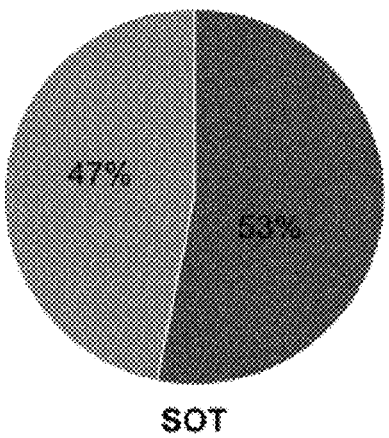
SOT
■ intact label
■ comp. ion cluster
Figure 3B
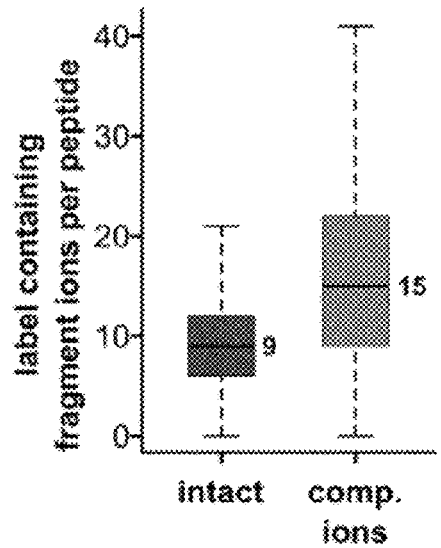
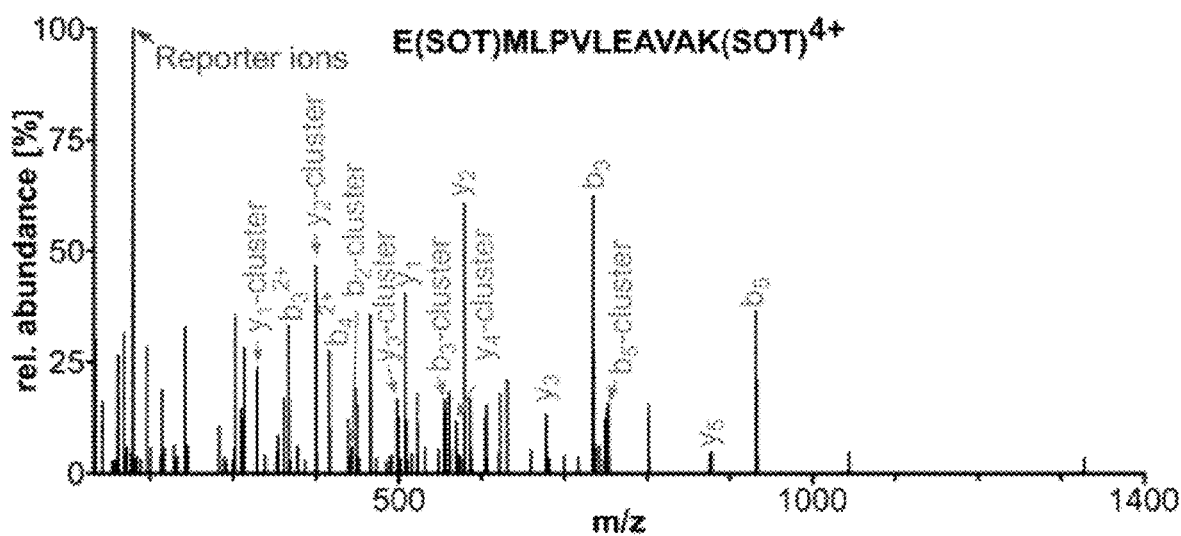
Figure 3C

SULFOXIDE-BASED REAGENT FOR MASS SPECTROMETRY

CROSS-REFERENCE TO RELATED APPLICATIONS

This application is a continuation of International Application No. PCT/EP2018/073812 filed Sep. 5, 2018, which claims priority to European Application No. 17190147.3 filed Sep. 8, 2017, the disclosures of which are hereby incorporated by reference in their entirety.

SUMMARY OF THE INVENTION

The present invention relates to sulfoxide-based reagents suitable in the mass spectrometric determination of analyte molecules such as peptides as well as adducts of such reagents and analyte molecules and applications of said reagents and adducts. Further, the present invention relates to methods for the mass spectrometric determination of analyte molecules.

BACKGROUND OF THE INVENTION

After the development of new genome sequencing methods that allow human genomics studies in just a few hours,[1] today, we are witnessing the emergence of novel mass spectrometry methods that now enable the investigation of the complete proteomes of cells and tissues.[2-4]

The proteome is defined as the collection of all proteins present in a sample and hence proteomes differ dramatically from cell type to cell type and in different tissues.[5]

Proteomics data therefore provide fingerprint-type information about cellular situations and potentially existing disease states.[6] To gain deep insight into the proteome of biological systems, it is necessary to obtain quantitative information about the levels of the individual proteins in the different samples. Nowadays, this is performed with mass spectrometry. Since exact quantification of intact proteins is difficult, the methods require digestion (trypsination) of the proteomes to give the corresponding peptides. For quantification of these peptides, methods such as metabolic labelling,[7-8] label-free quantification[9] or isobaric labelling[10-11] are performed.

Since isobaric labelling is able to reveal even small differences in peptide abundances and because many samples can be compared in one measurement, it is one of the most commonly used quantification methods.[12]

There is, however, still a need of increasing the sensitivity of MS analysis methods, particularly for the quantitative analysis of peptides that have a low abundance or when only little materials (such as biopsy tissues) are available, by MS.

A major drawback of MS reagents available today is their low cleavage efficiency, which reduces the number of reporter ions and therefore, complementary ions, available for quantitative analysis.[13] Additionally, the cleavage between the reporter and balancer units reduces the charge state of the complementary ion peptide and this may lead to the formation of MS-invisible neutral species.

BRIEF DESCRIPTION OF THE FIGURES

FIG. 2A: Comparison of fragmentation efficiency between TMT 1 and SOT 2 on a peptide. At a normalized collision energy of 28% HCD, the SOT-labelled peptide fragments more readily and yields high reporter ion signals. Tag=reacted reagent.

FIG. 2B: Statistical analysis of the reporter ion SOT$^{180}$ relative intensities observed in the MS$^2$-experiment. The reporter ion exhibits an excellent visibility, enabling facile reporter ion quantification. C) Charge state distribution of precursor-peptides labelled with the TMT (1) or SOT (2) duplex. By using the SOT-reagent, higher charge states become more abundant, which should lead to more efficient fragmentation due to higher charge density.

FIG. 3A: Ratio of all the identified fragment ions (67720) containing either the intact label (reporter+balancer) or which show loss of the reporter ions, leading to the formation of complementary ion clusters.

FIG. 3B: Statistical analysis of the identified peptide species. On average, each peptide forms 15 individual complementary ions, which result in 7-8 complementary ion clusters. The number of peptide fragments containing the intact, uncleaved label ensures reliable peptide identification.

FIG. 3C: Example MS$^2$-spectrum of the labelled peptide EMLPVLEAVAK$^{4+}$, depicting the reporter ions (red), seven complementary ion clusters (orange) and fragment ions used for identification (grey).

DETAILED DESCRIPTION OF THE INVENTION

Figure 1A:
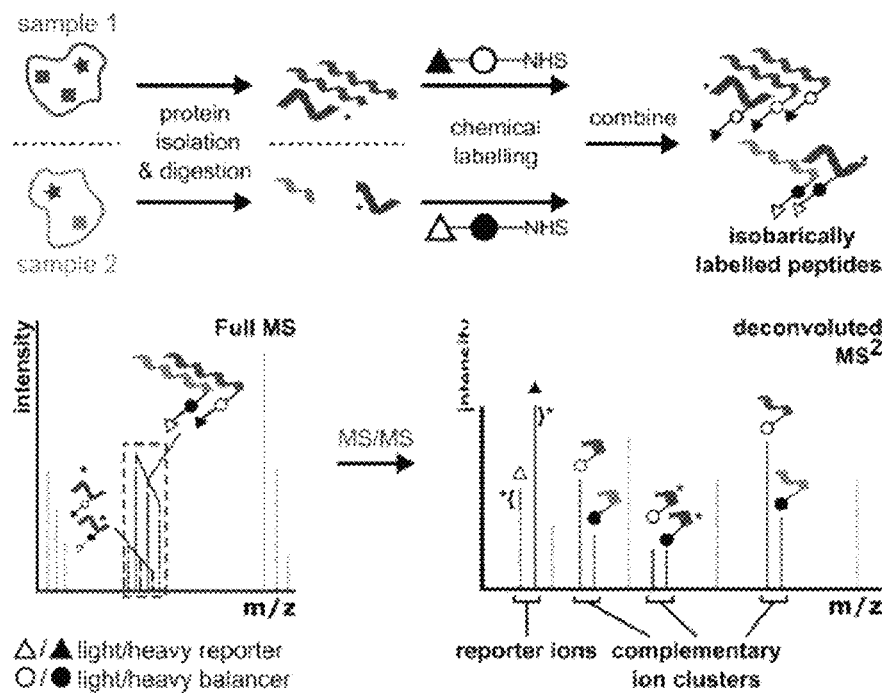
FIG. 1A: Isobaric labelling experiment for quantitative proteomics. The samples are individually labelled with isotopologues of the reagents 1 or 2 and combined for LC-MS. studies. Fragmentation in the gas phase yields reporter and complementary ions for relative quantification. The reporter ion ratio is distorted by co-isolated peptides (purple, *). The complementary ion clusters can be analysed without such a distortion.

Thus, the present invention relates to a novel sulfoxide-based reagent for use in MS which allows an extremely sensitive determination of analyte molecules such as peptides in biological samples. Further, the use of isotopically modified versions of the reagents allows to obtain accurate quantitative MS data for comparative studies. In particular, the inventive reagent may be used in proteomics enabling exact quantification of peptides in complex mixtures.

Thus, a first aspect of the present invention is a compound suitable as a reagent for mass spectrometry, which is of the general formula (I):

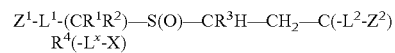

wherein
Z¹ is charge unit capable of carrying at least one charged moiety
L¹ is a bond or a spacer,
Z² is charge unit capable of carrying at least one charged moiety,
L² is a bond or a spacer,
$R^1, R^2, R^3, R^4$ are independently hydrogen or $C_1$-$C_3$ alkyl,
X is a reactive group capable of reacting with an analyte molecule, whereby a covalent bond with the analyte molecule is formed,
$L^x$ is a bond or spacer.

In a particular aspect, compound (I) may be present as an isotopologue, i.e. a compound wherein one or more main isotopes herein also referred to as isotopically neutral atoms of the compound, e.g. $^1H$, $^{12}C$, $^{14}N$ and/or $^{16}O$ atoms have been replaced by minor stable isotopes, i.e. stable isotopes such as D, $^{13}C$, $^{15}N$ and $^{18}O$. In particular preferred are $^{13}C$ and $^{15}N$.

The invention also relates to a reagent composition or reagent kit comprising at least one compound (I) and particularly a plurality of isotopically different species of such compound (I) which are preferably isobaric.

A further aspect of the invention is the use of compound (I) or a composition or kit comprising at least one compound (I) for the mass spectrometric determination of an analyte molecule, particularly of an analyte molecule comprising an amino-group such as a peptide or protein.

Still a further aspect of the invention is a covalent adduct formed by reaction of compound (I) and an analyte molecule. The adduct may be a compound of the general formula (II):

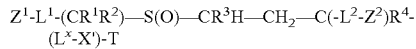

wherein
T is an analyte molecule,
X' is a moiety resulting from the reaction of a group X on the compound (I) with an analyte molecule T,
$Z^1, L^1, Z^2, L^2, L^x, R^1, R^2, R^3$ and $R^4$ are as defined in any one of other embodiments,
wherein the adduct may carry a permanent positive or negative charge.

The adduct of the compound of formula (I) and the analyte molecule, particularly an analyte molecule comprising a peptide moiety may be used for the mass spectrometric determination. The adduct may be generated by reacting the analyte molecule present in a sample with compound (I). The adduct, however, may also be provided as a pure substance for use as a calibrator and/or standard.

Still a further aspect of the invention is a method for the mass spectrometric determination of an analyte molecule in a sample comprising the steps:
(a) covalently reacting the analyte molecule with a compound of formula (I) as defined herein, whereby a covalent adduct of the analyte molecule and the compound (I) is formed, and
(b) subjecting the adduct from step (a) to a mass spectrometric analysis.

The present invention relates further to the determination of an analyte molecule by MS and in particular by quantitative MS. The analyte molecule may be any substance capable of forming a covalent bond with a reactive group X on the compound (I) of the present invention.

For example, the analyte may be a biomolecule selected from peptides, proteins, carbohydrates, amino acids, fatty acids, lipids, nucleosides, nucleotides, nucleic acids and other biomolecules including small molecule metabolites and cofactors as well as drugs, agricultural agents, toxins or metabolites thereof.

In general, analyte molecules may be present in biological, clinical or environmental samples such as body liquids, e.g. blood, serum, plasma, urine, saliva, etc., tissue or cell extracts, etc. In some embodiments of the present invention a full lysate of cells or tissue may be used without further purification. However, of course, the analyte molecules may be present in a sample which is a purified or partially purified sample, e.g. a purified or partially purified protein mixture or extract.

According to an especially preferred embodiment, the analyte molecule is a peptide or a protein, in particular a peptide or protein comprised in a complex sample. For example, the complete proteome of a cell or tissue may be analysed for the peptide or protein of interest within one MS measurement. Preferably, after isolation, the proteome, i.e. the collection of all proteins in a sample, is digested to provide smaller peptides before being labelled with a reagent described herein.

In particular preferred embodiments, the analyte molecule is a protein, peptide or substance having an amino group, which is capable of forming a covalent bond with reactive group X of compound (I). Such an amino group may be a N-terminal amino group of peptide chain and/or an amino group of a side chain, as for example of lysine.

According to another embodiment, the analyte molecule comprises at least one thiole, which is capable of forming a covalent bond with reactive group X of compound (I), such as Cys-containing peptides.

Of course, peptides or proteins to be analysed may also comprise post-translational modifications such as glycosylation, acylation etc. Such residues added to proteins by posttranslational modification may be also targeted by the inventive reagent.

Further, the analyte molecule may be also a carbohydrate or substance having a carbohydrate moiety, e.g. a glycoprotein or a nucleoside. For example, the analyte molecule may be a monosaccharide such as ribose, desoxyribose, arabinose, ribulose, glucose, mannose, etc., or an oligosaccharide, e.g. a disaccharide such as sucrose, maltose or lactose or a tri- or tetrasaccharide as well as a polysaccharide, or substance comprising such a mono-, oligo- or polysaccharide moiety.

The analyte molecule may comprise a carbonyl group, e.g. an aldehyde or a keto group, or a masked aldehyde or keto group, e.g. a hemiacetal group, particularly a cyclic hemiacetal group, which is capable of forming a covalent bond with reactive group X of compound (I). The analyte molecule may also comprise an acetal group, which can be converted into an aldehyde, keto or hemiacetal group before reaction with the compound (I).

Compound (I) of the present invention comprises a reactive group X capable of reacting with an analyte molecule, whereby a covalent bond with the analyte molecule is formed. In a preferred embodiment, group X is selected form
(i) a carbonyl-reactive group, which is capable of reacting with any type of molecule, e.g. carbohydrate molecule, having a carbonyl group,
(ii) a thiol-reactive group, which is capable of reacting with any type of molecule, e.g. Cys-containing peptide, having a thiol group or
(iii) an amine-reactive group, which is capable of reacting with any type of molecule, e.g. amino group-containing peptide, having an amino group.

Especially preferred are amine-reactive groups.

The carbonyl-reactive group may have either a super-nucleophilic N atom strengthened by the α-effect through an adjacent O or N atom $NH_2$—N/O or a dithiol molecule. It may be selected from:

(i) a hydrazine group, e.g. a $H_2N$—NH—, or $H_2N$—$NR^1$— group,
wherein $R^1$ is aryl, or $C_{1-4}$ alkyl, particularly $C_1$ or $C_2$ alkyl, optionally substituted e.g. with halo, hydroxyl, and/or $C_{1-3}$ alkoxy, (ii) a hydrazone group, e.g. a $H_2N$—NH—C(O)—, or $H_2N$—$NR^2$—C(O)— group,
wherein $R^2$ is aryl or $C_{1-4}$ alkyl, particularly $C_1$ or $C_2$ alkyl, optionally substituted e.g. with halo, hydroxyl, and/or $C_{1-3}$ alkoxy, (iii) a hydroxylamino group, e.g. a $H_2N$—O— group, (iv) a dithiol group, particularly a 1,2-dithiol or 1,3-dithiol group.

Of course, a hydrazine or hydroxyl amino group as described above may also be used to react with other electrophilic groups present on an analyte molecule.

The thiol-reactive group may be, for example, an electrophilic alkene group, e.g. $R^1R^2C$=$CR^3$—C(O)—NH— wherein $R^1$, $R^2$ and $R^3$ are independently H, halogen or $C_{1-4}$ alkyl, preferably H. Further thiol-reactive agents may be maleimides, alkyl halides or haloacetamides, in particular iodoacetamides.

There are numerous amino-reactive groups that can form chemical bonds with primary or secondary amines such as N-terminal amino-groups of peptides or proteins and methylated amines e.g. from methylated lysine side chains. Thus, according to the present invention "amino-reactive group" includes acyl azides, isothiocyanates, isocyanates, NHS esters, pentafluorphenylesters, hydroxybenzotriazole esters, sulfonyl chlorides, glyoxals, epoxides, oxiranes, carbonates, aryl halides, imidoesters, carbodiimides, anhydrides, and fluorophenyl esters.

However, according to preferred embodiments, the "amino-reactive" group used herein, is preferably an active ester group such as N-hydroxy succinimide (NHS) or sulfo-NHS, a hydroxybenzotriazole (HOBt), a 1-hydroxy-7-azabenzotriazole (HOAt) group or an imidoester —$CH_2$—C(=$NH_2^+$)—O—$CH_3$. Particular preferred is NHS.

The compound (I) has charge units $Z^1$ and $Z^2$ each capable of carrying at least one charged moiety, i.e. the charge units $Z^1$ and $Z^2$ may be permanent charged e.g. when using a quaternary ammonium group, or may be generated by protonation (positive charge) or deprotonation (negative charge).

Preferably $Z^1$ and $Z^2$ are equal and/or $Z^1$ and $Z^2$ have the same charge.

In particular embodiments, but not necessarily, compound (I) has a charge units $Z^1$ and $Z^2$ each comprising at least one charged moiety, i.e. a moiety which is predominantly present in a charged state under substantially neutral conditions.

For example, the charge units $Z^1$ and $Z^2$ may each comprise (i) at least one positively charged moiety such as a primary, secondary, tertiary or quaternary ammonium group or a phosphonium group, particularly having a p$K_a$ of 10 or higher, more particularly having a p$K_a$ of 12 or higher, or (ii) at least one negatively charged moiety such as a phosphate, sulphate, sulphonate or carboxylate group, particularly having a p$K_b$ of 10 or higher, more particularly having a p$K_b$ of 12 or higher.

According to an preferred embodiment $Z^1$ and $Z^2$ are both tert-amino groups, i.e. —$NR^1R^2$ with $R^1$ and $R^2$ preferably being $C_1$-$C_5$-alkyl or forming an 5- or 6 membered cyclic alkyl ring optionally comprising one or two further heteroatoms, such as N. $R^1$ and $R^2$ may be selected independently but preferably $R^1$ and $R^2$ are equal. Especially $R^1$ and $R^2$ are selected from dimethyl-amino and diethyl-amino or form together piperidine or pyrolidine.

Such protonation of $Z^1$ and $Z^2$ can be done as a last step of the synthesis of inventive reagents and the protonated reagent may be stored. However, $Z^1$ and $Z^2$ may be also protonated in the gas phase, even after reaction of the inventive reagent with an analyte molecule, directly before MS-analyses which is even preferred. By protonation of $Z^1$ and $Z^2$ formation of neutral species during reagent cleavage is avoided.

Groups $L^1$, $L^2$ and $L^x$ in general formula (I) independently represent a bond, i.e. a covalent bond, or a spacer, i.e. a linear or branched spacer having a chain length from 1 up to usually 4, 6, 8 or 10 atoms or even more, e.g. C-atoms optionally including at least one heteroatom, in particular N, and or carbonyl groups. Preferably $L^1$ and $L^2$ are equal with regard to chain length and optionally included heteroatoms and/or carbonyl groups, however, may differ with isotope composition, i.e. $L^1$ and $L^2$ may be isotopologues to each other.

According to an especially preferred embodiment $L^1$ and/or $L^2$ groups are —C(O)—NH—$(CH_2)_n$ and/or —NH—C(O)—$(CH_2)_m$— with m and n are an integer between 1 and 10.

In a preferred embodiment, the compound of formula (I) is suitable as a reagent for the determination of peptide or protein molecules and may be a compound of the general formula (Ia):

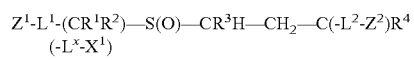

wherein $Z^1$ comprises at least one positively charged moiety such as a primary, secondary, tertiary or quaternary ammonium group, in particular a protonated tert-amino group, such as protonated dimethyl-amino and diethyl-amino, piperidin or pyrolidin, $L^1$ is a spacer, in particular —C(O)—NH—$(CH_2)_n$— with n being an integer from 1 to 10, wherein n is preferably m, $Z^2$ is equal to $Z^1$, $L^2$ is a spacer, in particular —NH—C(O)—$(CH_2)_m$— with m being an integer from 2 to 10, $R^1$, $R^2$, $R^3$, $R^4$ are hydrogen, $X^1$ an amine reactive group which is capable of reacting with an amine, e.g. an amino group of an analyte molecule such as an peptide, $L^x$ is a bond or spacer.

$X^1$ is preferably selected from N-hydroxy succinimide (NHS), sulfo-NHS, hydroxybenzotriazole (HOBt), 1-hydroxy-7-azabenzotriazole (HOAt) or imidoesters —$CH_2$—C(=$NH_2^+$)—O—$CH_3$.

A specific example of a compound according to the present invention is a compound of formula (Ib):

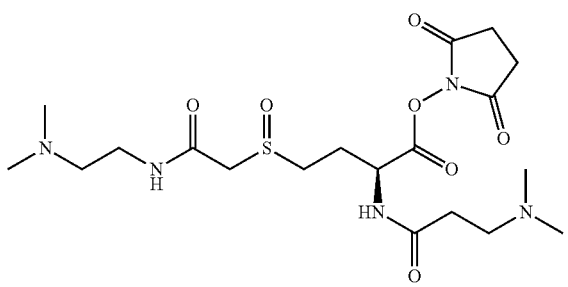

A further aspect of the present invention relates to a compound of formula (I) which is an isotopologue. The term "isotopologue" relates to a compound (I) wherein at least one of the main isotopes is replaced by a stable minor isotope of the respective element, having a molecular mass, which is different from the molecular mass of the respective main isotope. Thus, the resulting isotopologue of (I) has a molecular mass which is different from the molecular mass of the respective compound consisting of the main isotopes here referred to isotopically neutral. This difference in molecular mass allows mass spectrometric differentiation of an isotopically neutral compound and an isotopologue thereof. In a preferred embodiment, the isotopologue comprises at least one isotope selected from D (as replacement of H), $^{13}C$ (as replacement of $^{12}C$), $^{15}N$ (as replacement of $^{14}N$) and $^{18}O$ (as replacement of $^{16}O$).

In an isotopologue, one or more and up to all of the respective isotopically neutral atoms may be replaced by isotopes. Thereby, a great number of different isotopologues of a single compound may be provided.

For example, in a compound of formula (Ia) or (Ib) as shown above, one or more or all $^{14}N$ and $^{12}C$ atoms in the $L^1$ spacer, respectively —C(O)—NH—$(CH_2)_n$ with preferably n=m, and/or the $L^2$ spacer, respectively —NH—C(O)—$(CH_2)_m$— with preferably m>1, may be replaced by $^{15}N$ or $^{13}C$.

The compound (I) may be provided as an isotopically neutral compound or as an isotopologue which is MS-distinguishable from the respective isotopically neutral compound or as a composition comprising a plurality of different MS-distinguishable isotopologues of the same compound or as a kit comprising a plurality of different MS-distinguishable isotopologues of the same compound in separate form. Composition or kits comprising a plurality of different MS-distinguishable isotopologues of a reagent are particularly suitable for multiplexing applications as described below.

In a preferred embodiment of the invention a composition or kit comprises at least two isotopologues reagents as described herein which are isobaric. For example, into a first reagent A according to formula (I) a heavy stable isotope such as $^{15}N$ or $^{13}C$ is introduced into $Z^1$ or $L^1$. $Z^2$ and $L^2$ remain unchanged. In a second reagent B $Z^1$ and $L^1$ remain unchanged, but the same isotope like in reagent A is introduced into $Z^2$ or $L^2$. The resulting agents A and B are isobaric (see also FIG. 1).

The reagent according to formula (Ib) allows the introduction of up to seven heavy stable isotopes such as $^{15}N$ or $^{13}C$ into the structures generating reporters with Δ m/z=1 while keeping isobaricity.

Due to the isobaric character of the reagents the same analyte molecules derived from two samples will feature as adduct the same retention time during MS-separation. Entering the mass spectrometer at the same time, the adducts derived from different samples and labelled with different but isobaric inventive reagents lead to one indistinguishable m/z value in a MS screen. This allows performing mass spectrometry-based identification by selecting a single precursor m/z for $MS^2$.

Thus, kits or compositions comprising reagents of formula (Ib) having 1 to 7 stable isotopes introduced while being isobaric represent another preferred embodiment of the present invention. Such a design enables mass spectrometric quantification of up to 8 different samples in parallel with one single MS measurement.

The synthesis of preferred compounds of formula (I) including isotopologues thereof is described below in the Examples section and FIG. 4.

Still a further aspect of the invention relates to the use of the compound of formula (I) for the mass spectrometric determination of an analyte molecule, particularly for the determination of a peptide analyte molecule as described above. This use involves a derivatization of the analyte molecule by means of a reaction with compound (I), whereby a covalent adduct is formed and subsequently subjected to analysis by MS.

A general scheme involving the use of compound (I) as a reagent for the quantitative determination of an peptide molecule by MS is shown in FIG. 1. In particular, a reagent according to the present invention (Formula 1b; SOT) is compared to a reagent known from the prior art.

In case the adduct comprises a positive charge, MS detection occurs in the positive mode. In case the adduct has a negative charge, the detection will be performed in the negative MS mode.

Mass spectrometric determination may be combined by additional analytic methods including chromatographic methods such as gas chromatography (GC), liquid chromatography (LC), particularly HPLC, and/or ion mobility-based separation techniques.

A further aspect of the invention is an adduct formed by reaction of the compound of general formula (I) as described above and an analyte molecule. By means of this reaction, a covalent bond between compound (I) and the analyte molecule is formed.

In a preferred embodiment, the adduct is a compound of the general formula (II):

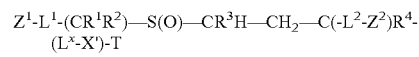

wherein

T is an analyte molecule,

X' is a moiety resulting from the reaction of a group X on the compound (I) with an analyte molecule T, $Z^1$, $L^1$, $Z^2$, $L^2$, $L^x$, $R^1$, $R^2$, $R^3$ and $R^4$ are as defined above, wherein the adduct may carry a permanent positive or negative charge.

For MS detection, the adduct compound of formula (II) carries a positive or negative charge. This charge is preferably provided by the charge units $Z^1$ and $Z^2$ of compound (I), preferably by protonation of $Z^1$ and $Z^2$. The presence of a charge in compound (I), however, is not necessary since a charge can be provided by other means, e.g. when the analyte molecule itself carries a charge and/or when the adduct can be provided with a charge by means of a protonation or deprotonation.

The presence of two charge units $Z^1$ and $Z^2$, preferably protonated tert-amino groups, leads to higher charge states which result in high analyte molecule/adduct fragmentation and hence more accurate analyte molecule identification. Moreover, the presence of the two charged units $Z^1$ and $Z^2$ avoids the formation of neutral species during adduct cleavage/fragmentation. The increased charge density facilitates detection and fragmentation.

Still a further aspect of the invention is the use of the adduct compound (II) for the mass spectrometric determination of an analyte molecule. In a particular preferred embodiment, the mass spectrometric determination comprises tandem mass spectrometric determination, more particularly in a triple quadrupole device, wherein the molecule ion of the analyte adduct is subjected to fragmentation, e.g. by collision-induced dissociation (CID).

During fragmentation in addition to a reporter ion comprising $Z^1$ and $L^1$ a balancer-adduct conjugat, the complementary ion, is generated from arch adduct (see also FIG. 1) with the balancer comprising $Z^2$ and $L^2$. The attached balancer retains the distinct isotope pattern from the isobaric labelling reagents, thus, the complementary ion allowing quantification as well. This provides the advantage that co-eluting peptides which give reporter ions indistinguishable from the reporter signals of interest, can not disturb the signal. Desirably, the known problem of ratio distortion hindering an accurate quantification based on reporter ion analysis can thus be overcome.

In one embodiment, the adduct compound (II) may be generated by reaction of an analyte molecule present in a sample to be analysed with compound (I) which has been added to the sample.

In a further embodiment, an adduct compound (II) may also be provided as a pure substance for use as a calibrator and/or as a standard. Use of the adduct compound (II) as a calibrator may involve generating a calibration curve for a specific analyte molecule, wherein different known amounts of adduct compound (II) are subjected to MS analysis and the respective signal intensities are measured in order to allow an accurate quantitative determination of an unknown amount of the analyte molecule present in a sample.

Still a further aspect of the present invention relates to a method for the quantitative mass spectrometric determination of an analyte molecule comprising the steps:
(a) providing at least two analyte samples to be compared,
(b) covalently reacting the analyte molecule in each provided sample with a reagent of general formula (I) as defined herein, whereby for each sample a different isotopologous reagent of general formula (I) is used and whereby the isotopologues reagents used for different samples are isobaric to each other, and whereby an adduct of the analyte molecule and the reagent in each sample is formed,
(c) combining the at least two samples comprising the adduct of the analyte molecule and the isobaric reagents,
(d) subjecting the combined adducts from step (c) to a mass spectrometric analysis, wherein the mass spectrometric analysis step (d) preferably comprises:
(i) subjecting ions of the combined isobaric adducts to a first stage of mass spectrometric analysis, whereby the ions of the combined adducts are characterised according to their mass/charge (m/z) ratio,
(ii) causing fragmentation of the combined adduct ions, whereby a reporter ion and a complementary ion having the same charge are yielded from each adduct ion and whereby non-isobaric reporter ions and non-isobaric complementary ions are provided for each originally provided analyte sample to be compared,
(iii) subjecting the non-isobaric reporter ions and non-isobaric complementary ions of step (ii) to a second stage of mass spectrometric analysis,
(iii) relative quantification of the reporter ions of step (ii), and
(iv) relative quantification of the complementary ions of step (ii).

Of course, one of the analyte samples of step (a) may be a standard or reference sample. In this way, the amount of analyte in one unknown sample can be determined. However, according to the inventive method the same analyte of a plurality of samples can also be quantified within one MS measurement and the analyte content of the different samples be compared.

The present invention is suitable for clinical applications such as providing diagnostic and/or prognostic information on a subject, particularly a human subject. Specific applications are diagnosis of diseases associated with, accompanied by or caused by an alteration in the proteome of a cell or tissue, for example the diagnosis of hyperproliferative diseases such as cancer, e.g. determination of the aggressiveness and invasiveness of tumors, characterization of platelets as well as measurement of the level of liver fibrosis, investigation of antibody characteristics and characteristics of immune cells such as T-cells. In general, the reagent (I) and its isotopologues can be used to obtain quantitative information about the presence and levels of specific protein or peptides in cells and/or tissues.

EXAMPLES

1. Introduction

Figures 1B, 1C:
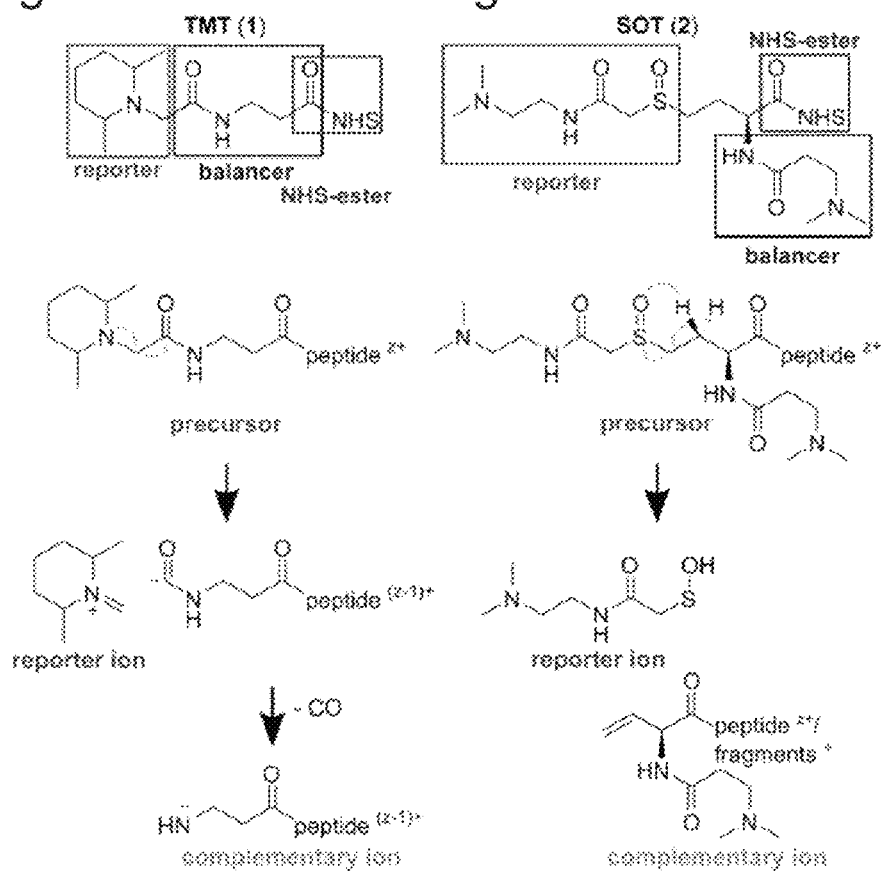
FIG. 1B: Currently used TMT (1) reagent. Fragmentation introduces a negative charge on the balancer, reducing the overall charge state on the complementary ions. C) SulfOxide Tag (SOT, 2) reported in this study with a charge-neutral fragmentation that retains all charges on the complementary ions to facilitate fragmentation.

The proteomes of two samples are isolated, digested and the peptides are reacted with an isobaric labelling reagent such as the TMT 1 (FIG. 1B) or the inventive labelling reagent 2 (FIG. 1C).

The prepared derivatized peptide mixtures are next combined and the mixture is analysed by HPLC-MS[14] or even CE-MS.[15-16]

During separation, the same peptides derived from the two samples (blue and red in FIG. 1) will feature the same retention time due to the isobaric character of the labels. They will consequently enter the mass spectrometer at the same time, leading to one indistinguishable m/z-value in the full MS-scan. This allows performing mass spectrometry-based identification by selecting a single precursor m/z for $MS^2$. Cleavage of the isobaric labels provides now two different reporter ions (Δ, FIG. 1A), which allows relative quantification.

In addition to a reporter ion, a balancer-peptide conjugate, the complementary ion, is also generated from each peptide. Because the attached balancer retains the distinct isotope pattern from the isobaric labelling reagent, the complementary ions allow quantification as well.[13]

This even has the advantage that co-eluting peptides (purple), which give reporter ions indistinguishable from the reporter signals of interest, can not disturb the signal. This problem, known as ratio distortion, often hinders accurate quantification based on reporter ion analysis.[17]

A drawback of reagents available today is their low cleavage efficiency, which reduces the number of reporter ions and therefore, complementary ions, available for analysis.

Additionally, the cleavage between the reporter and balancer units reduces the charge state of the complementary ion peptide and this may lead to the formation of MS-invisible neutral species.

2. Results and Discussion

Here we report the development of a new SulfOxide Tag reagent 2 (SOT, FIG. 1) that fragments cleanly and with high yield. Strong signals for both the reporter and the complementary ions are generated based on a sulfoxide fragmentation in the gas phase. Importantly, the reagent features two basic tert-amino groups, which are protonated in the gas phase. This avoids formation of neutral species during reagent cleavage. In contrast, it even increases the charge density, which facilitates detection and fragmentation. The SOT reagent 2 allows in principle the introduction of up to seven heavy stable isotopes into the structure generating reporters with $\Delta m/z=1$, while keeping isobaricity. This design was chosen to enable mass spectrometric quantification of eight different samples in parallel with one single measurement.

Figure 4A:
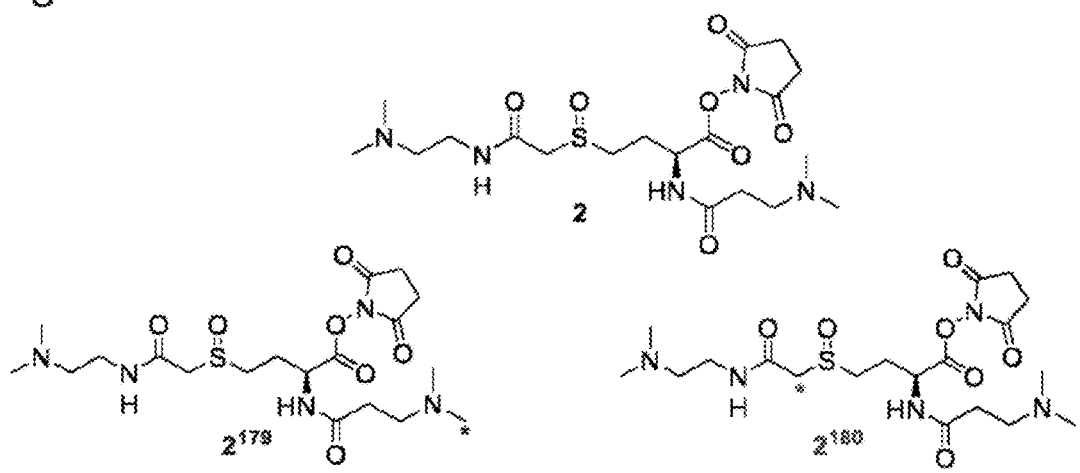
FIG. 4A: Depiction of the inventive reagent 2 and of the isotopologues $2^{179}$ and $2^{180}$.
Figure 4B:
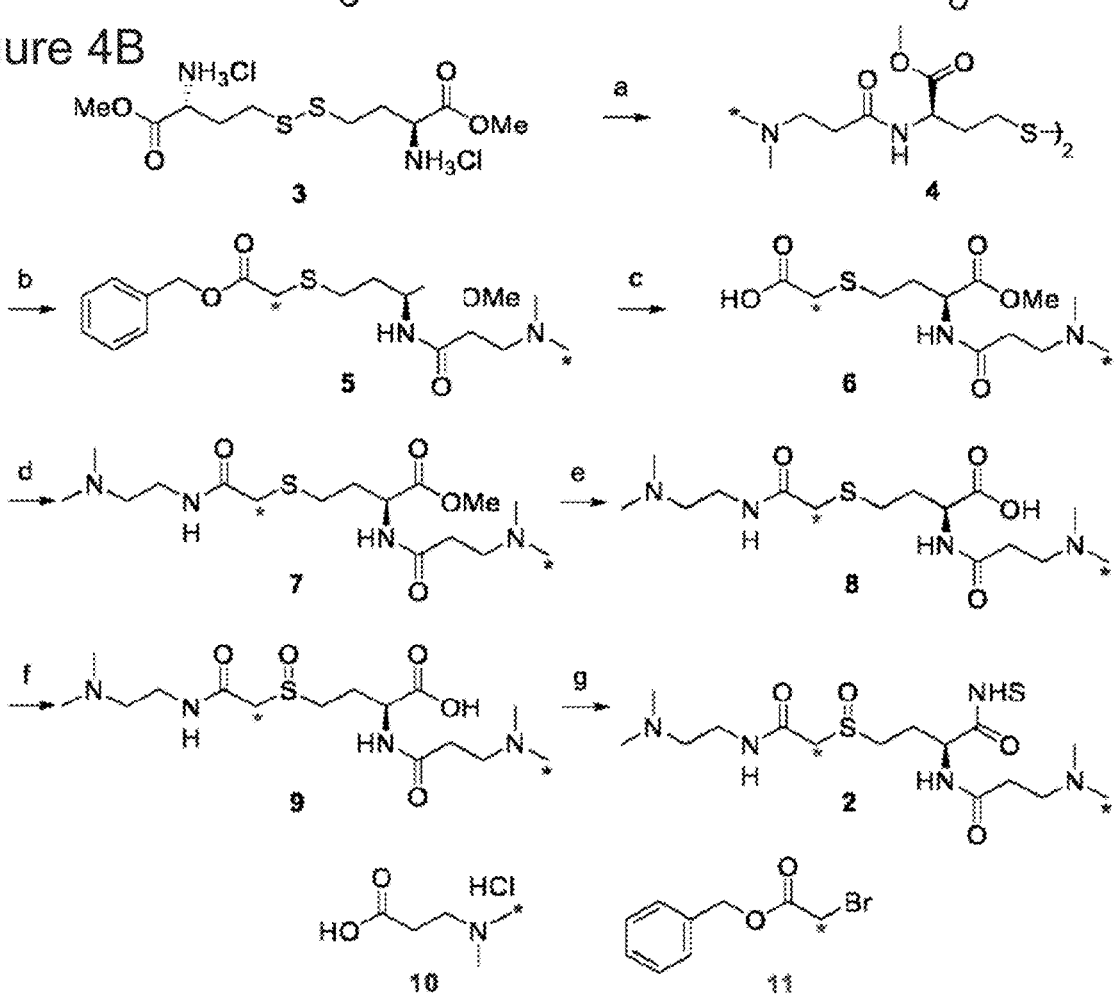
FIG. 4B: a) 3-(Dimethylamino)propionic acid hydrochloride, NEt$_3$, HOBt, 60° C., 2 h, 85%; b) Over two steps in situ i) TCEP*HCl, NaHCO$_3$, H$_2$O/DMF (4:1), r.t., 10 min; ii) Benzyl bromoacetate, r.t., 2 h, 95%; c) 10% Formic acid in MeOH, 100 wt % Pd black, 40° C., 2 h, 81%; d) N,N-dimethylethane-1,2-diamine, DIPEA, PyBOP, DMF, 40° C., 1 h, 73%; e) LiOH, MeOH/H$_2$O (2.5:1), r.t., 1 h, 100%; f) pH=2, mCPBA, H$_2$O, r.t., 20 min, 75%; g) NHS-TFA, pyridine, DMF, r.t., 2 h, 35%. 179 Da and 180 Da are the molecular weights of the generated reporter ions.

The synthesis of the inventive reagent 2 and of two isobaric isotope derivatives ($2^{179}$ and $2^{180}$), which feature different reporter ion molecular weights (179 Da and 180 Da), is shown in FIG. 4 (cf. also item 4. of the Examples). The synthesis starts with the methylester of the homocystine dimer 3, which is first converted with dimethylamino propionic acid into the bis-amide 4. Reduction of the disulfide and alkylation of the thiol with benzyl bromoacetate furnishes the key intermediate 5. Cleavage of the benzylester to 6 and reaction of 6 with 1,1-dimethylethylenediamine gives the bisamide 7. Saponification of the methylester in 7 to 8, oxidation of the sulfide to the sulfoxide 9 and conversion of the acid provides reagent 2 as the active ester. To access the needed isotopologues, we replaced in a second synthesis the dimethylamino propionic acid by the same compound 10 in which one methyl group carries a $^{13}C$ atom (SI). In a third synthesis, we used the $^{13}C$-labelled benzylbromoacetate 11 (SI). This gave the corresponding reagents $2^{179}$ and $2^{180}$ in similar yields.

To examine the fragmentation properties of inventive reagent SOT 2, we digested a full *E. coli* lysate, containing all translated proteins into the corresponding peptides following a standard protocol (SI). The obtained complex peptide mixture (P) was divided into two portions. While one portion was reacted with reagent $2^{179}$ (P-$2^{179}$) the other was combined with $2^{180}$ to give P-$2^{180}$ (pH=8.5, 150 mM triethylammonium bicarbonate buffer, 3 mg 2, 60 min). We subsequently quenched unreacted reagent 2 with hydroxylamine. Next, the labelled mixtures {P-$2^{179}$+P-$2^{180}$} were combined in a 1:1 ratio, and the complex mixture was desalted and concentrated according to reported procedures.[18]

For comparison, we performed the same experiment with the commercially available isotopically labelled TMT reagents 1 (duplex) according to manufacturer's recommendations to obtain the mixture {P-TMT$^{126}$+P-TMT$^{127}$}. The peptide mixtures {P-$2^{179}$+P-$2^{180}$} and {P-TMT$^{126}$+P-TMT$^{127}$} were next measured by nanoHPLC-MS$^2$ and the data were analysed using the MaxQuant software and a software package developed in-house (SI).[19] The obtained data are depicted in FIG. 2 and FIG. 3.

As one example, FIG. 2A shows the cleavage of the SOT reagent 2 after reaction with the peptide ALEG-DAEWEAK$^{2+}$ (two labels) in direct comparison to the corresponding TMT labelled peptide in the complex mixture. We measured at a normalized fragmentation energy of 28% HCD (higher-energy collisional dissociation), which is ideally suited to fragment peptides for their identification. The SOT reagent 2 clearly generates more reporter ions and in addition, the reagent seems to support the peptide fragmentation because we observe more fragment ions. FIG. 2B shows an analysis of all peptides identified in the SOT-labelled sample and here, we see that in the majority of MS$^2$-spectra, the relative reporter ion intensity is as high as 80-100%, which is unprecedented.

This enables easy relative quantification by determining reporter ion ratios with available software packages. FIG. 2C shows the charge states of the intact labelled peptides before fragmentation (precursors). In agreement with our design, we see that the SOT reagent 2 generates labelled peptides with much higher charge states. Importantly, more than 60% of the labelled peptides have charge states equal to or above +3. This high charge density facilitates the subsequent fragmentation, which results in more data for exact analysis.

While the reporter ion intensity allows measuring the relative ratios between all peptides present in P-$2^{180}$ versus P-$2^{179}$, it is often desirable to quantify with the complementary ion clusters generated by the balancer-peptide conjugates. Because these balancer-conjugates fragment further in the mass spectrometer, a large number of complementary ion clusters are formed, which are sequence-specific and can all be used for quantification. This provides higher data density and it avoids the problems associated with ratio distortion. In our experiment, we observe that the SOT reagent 2 has almost perfect properties for such a complementary ion cluster analysis. When we studied the label-containing peptide fragment ions, we saw that 53% of these fragments still contained the intact reagent 2, while 47% have lost the reporter group yielding complementary ion clusters (FIG. 3A). This near perfect 1:1 ratio allows for the parallel identification of the (intact) peptides with standard database search algorithms and quantification via the abundantly formed complementary ion clusters. FIG. 3B shows that the SOT reagent 2 creates from every precursor on average 15 peptide-balancer fragments for later quantification, which corresponds to approximately 7-8 complementary ion clusters. FIG. 3C shows the spectrum from one peptide as an example. The signals for the reporter ions (red) and of seven complementary ion clusters (orange), encompassing 14 complementary ions, are clearly visible in high relative intensities. For identification of the peptide, multiple high intensity ions are available (grey).

3. Conclusion

In summary, we report the design of a new isobaric labelling reagent that allows the efficient parallel formation of reporter ions and complementary ion clusters for precise peptide quantification. The reagent helps to eliminate quantification errors caused by ratio distortion. This enables for the first time accurate determination of relative peptide and hence protein abundances even in complex samples. The most important properties of the SOT reagent 2 are that reporter ions and complementary ion clusters are formed in parallel and that the introduction of multiple tert-amino groups generates the expected higher charge states which results in better peptide fragmentation and hence more accurate peptide identification.

4. Chemical Synthesis Procedures 4.1 Synthesis of Starting Materials

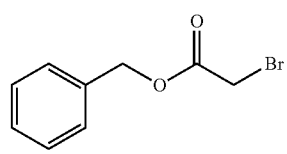 [SMILES: O=C(CBr)OCc1ccccc1]

Benzyl Bromoacetate (12) Typical Procedure 1 (TP1)

To a dry and Ar-flushed 50 mL Schlenk-flask, equipped with a stirring bar and a septum, was added the commercially available bromoacetic acid (1.00 g, 7.19 mmol, 1.16 equiv), phenylmethanol (0.64 mL, 6.20 mmol, 1.00 equiv) and 4-methylbenzene-1-sulfonic acid (21.36 mg, 0.12 mmol, 0.02 equiv) in the present of 10 mL toluene refluxed for 2 h. After completion, the reaction mixture was cooled to rt and washed twice with 20 mL 20% sodium bicarbonate solution in water followed by brine and water wash. The combined organic layers were dried over magnesium sulfate and concentrated via vacua Purification by flash column chromatography (silica gel, EtOAc/DCM 1:4) yielding 12 as a colourless oil (1.38 g, 84%).

$^1$H-NMR (400 MHz, methanol-$d_4$) δ=7.46-7.13 (m, 1H), 5.16 (s, 1H), 3.95 (s, 6H) ppm.

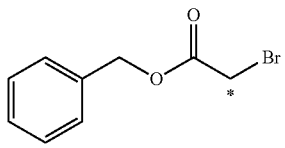 [SMILES: O=C(CBr)OCc1ccccc1]

Benzyl bromo(2-$^{13}$C)acetate (11)

Following TP1, bromoacetic acid-2-$^{13}$C (500 mg, 3.60 mmol, 1.16 equiv) and phenylmethanol (0.32 mL, 3.10 mmol, 1.00 equiv) reacts with 4-methylbenzene-1-sulfonic acid (10.68 mg, 0.06 mmol, 0.02 equiv) in the present of 5 mL toluene 2 h reflux and was worked-up as usual. Purification by flash column chromatography (silica gel, EtOAc/DCM 1:4) yielding 11 as a colourless oil (427 mg, 52%).

$^1$H-NMR (400 MHz, methanol-$d_4$) δ=7.41-7.33 (m, 5H), 5.20 (s, 2H), 4.18 (s, 1H), 3.80 (s, 1H) ppm. HRMS (EI$^+$): calc. for $C_8^{13}CH_{10}BrO_2^+$ [M+H]$^+$: 229.9819; found: 229.9718. IR (cm$^{-1}$): ṽ=3065, 1733, 1587, 1497, 1455, 1376, 1278, 1213, 1147, 1106, 967, 736.

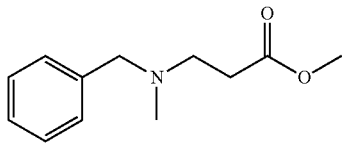

Methyl 3-[benzyl(methyl)amino]propanoate (13)

Methyl-3-bromopropanoate (3.00 g, 18.0 mmol) and N-methyl-1-phenylmethanamine (2.18 g, 18.0 mmol) were dissolved in acetonitrile (120 mL). After 2 min stirring at rt, Na$_2$CO$_3$ (19.0 g, 180 mmol) was added and the temperature were increased to 70° C. for 24 h. After cooling, the reaction solution was filtered, and 120 mL DCM was added to the filtrate. The organic phase was washed with 0.5 M NaOH (3×50 mL) and dried over Na$_2$SO$_4$. After filtration, the product was concentrated at reduced pressure to yield 13 as colourless oil (3.44 g, 16.5 mmol 92%).

$^1$H NMR (400 MHz, CDCl$_3$): δ 7.30-7.18 (m, 5H, C$_6$H$_5$—CH$_2$—N), 3.63 (s, 3H, —COOCH$_3$), 3.48 (s, 2H, C$_6$H$_5$—CH$_2$—N), 2.71 (t, J=7.2 Hz, 2H, —N—CH$_2$—CH$_2$—), 2.49 (t, J=7.2 Hz, 2H, —CH$_2$—COOCH$_3$), 2.17 (s, 3H, —N—CH$_3$). $^{13}$C NMR (101 MHz, CDCl$_3$): δ 173.00 (—COOCH$_3$), 138.85 (q), 128.95, 128.24 and 127.04 (C$_6$H$_5$—CH$_2$), 62.12 (C$_6$H$_5$—CH$_2$), 52.75 (—N—CH$_2$—CH$_2$—), 51.56 (—COOCH$_3$), 41.91 (—N—CH$_3$), 32.75 (CH$_2$—COOCH$_3$). HRMS (ESI$^+$): calc. for $C_{12}H_{18}NO_2^+$ [M+H]$^+$: 208, 13321; found: 208.13313. IR (cm$^{-1}$): ṽ=2950 (w), 2841 (w), 2790 (w), 1737 (s), 1495 (w), 1452 (m), 1236 (m), 1357 (w), 1325 (w), 1202 (m), 1168 (s), 1125 (m), 1975 (w), 1038 (m), 1025 (m).

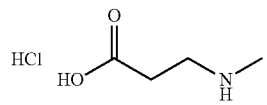

3-(Methylamino)propanoic Acid Hydrochloride (14)

In a flame-dried Schlenk tube methyl 3-[benzyl(methyl)amino]propanoate 13 (1 g, 4.82 mmol) was dissolved in MeOH (60 mL). Then the atmosphere of the tube was purged with N$_2$ and 10 wt % of Pd/C (100 mg) were added in small portions to the solution. The atmosphere was purged with N$_2$ again to make sure that no oxygen was left. A double-layered latex balloon filled with H$_2$ was attached to the Schlenk tube and the reaction was stirred for 16 h at room temperature. After 6 h and 10 h the balloon was refilled with H$_2$. Pd/C was filtered off with celite. Evaporation resulted in a yellowish oil. The crude volatile product was used without further purification for the next step. The resulting methyl ester was dissolved in 5 M HCl and refluxed for 8 h. The solution was evaporated to dryness. Recrystallization from MeOH/ethoxyethane yielded the desired product 14 as colourless hygroscopic crystals (478 mg, 3.42 mmol, 71%).

Mp.: 89-92° C. $^1$H-NMR (400 MHz, D$_2$O) δ 3.28 (t, J=6.4 Hz, 2H, —N—CH$_2$—CH$_2$—), 2.81 (t, J=6.5 Hz, 2H, —CH$_2$—COOH), 2.72 s (3H, CH$_3$) ppm. $^{13}$C NMR (101 MHz, CDCl$_3$): δ 174.11 (—COOH), 44.36 (—N—CH$_2$—CH$_2$—), 32.99 (—CH$_2$—COOH), 29.90 (CH$_3$) ppm. HRMS (ESI) calc. for $C_4H_{10}NO_2^+$ [M+H]$^+$: 104.07060; found: 104.07063. IR (cm$^{-1}$): ṽ=3376 (w), 2968 (s), 2819 (s), 1729 (s), 1557 (w) 1465 (m), 1402 (s) 1351 (w), 1289 (w), 1189 (s), 1156 (s), 1024 (s).

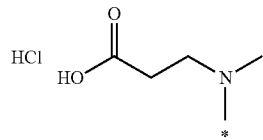

3-{Methyl[($^{13}$C)methyl]amino}propanoic Acid Hydrochloride

(10) 3-(methylamino)propanoic acid hydrochloride 14 (401 mg, 2.87 mmol, 1.00 equiv) was dissolved in 88% formic acid (1.79 mL, 44.8 mmol, 15.6 equiv). Then ($^{13}$C) formaldehyde (20% in water; 1 g, 6.45 mmol, 2.25 equiv) was added and the solution was heated via microwave irridation at 110° C., 100 W for 1 h. 200 μL HCl was added and the solvent was removed in vacuo. Traces of formic acid were removed azeotropically with toluene in vacuo. The slightly yellowish solid was recrystallized from MeOH/ethoxyethane to obtain a colourless solid (383 mg, 2.48 mmol, 86%).

Mp.: 183° C. $^1$H-NMR (400 MHz, D$_2$O): δ 3.30 (td, J=6.7, 3.0 Hz, 2H, —N—CH$_2$—CH$_2$—), 2.97-2.60 (m, 8H, —CH$_2$—COOH, —CH$_3$, —$^{13}$CH$_3$) ppm. $^{13}$C-NMR (101 MHz, D$_2$O): δ=174.06 (—COOH), 53.10 (—N—CH$_2$—CH$_2$—), 43.34 (—CH$_3$), 42.78 (—$^{13}$CH$_3$), 28.78 (—CH$_2$—COOH) ppm. HRMS (ESI$^+$): calc. for C$_4$$^{13}$CH$_{12}$NO$_2$$^+$ [M+H]$^+$ 119.08961, found 119.08960. IR (cm$^{-1}$): $\tilde{v}$=2957 (m), 2692 (m), 2592 (w), 2481 (w), 1717 (s), 1468 (w), 1420 (m), 1370 (w), 1300 (w), 1201 (s) 1161 (m), 1006 (w), 966 (m), 854 (s), 798 (m).

4.2 General Synthesis Procedures

In the following section compound 2$^{179}$ will be assigned as 2** and compound 2$^{180}$ will be assigned as 2*.

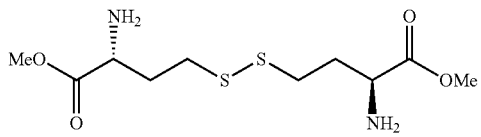 [SMILES: COC(=O)[C@H](N)CCSSCC[C@H](N)C(=O)OC]

Methyl (2R)-2-amino-4-{[(3S)-3-amino-4-methoxy-4-oxobutyl] disulfanyl} Butanoate (3)

A dry and Ar-flushed 250 mL Schlenk-flask, equipped with a stirring bar and a septum, was charged with the commercially available DL-homocystine (4,4'-disulfanediylbis(2-aminobutanoic acid), 6.0 g, 22.36 mmol, 1.0 equiv) dissolved in anhydrous MeOH (80 mL). The white slurry solution was cooled to 0° C. and thionyl chlorid (6.48 mL, 89.44 mmol, 4.0 equiv) was added dropwise via syringe. The resulting colourless reaction mixture was allowed to warm to rt over 3 h. Then, the reaction mixture was concentrated via vacuo over night yielding 3 as a white solid (6.6 g, 100%).

$^1$H-NMR (400 MHz, methanol-d$_4$) δ=4.21 (t, J=6.5 Hz, 2H), 3.86 (s, 6H), 3.35 (s, 2H), 2.84 (m, 5H), 2.47-2.22 (m, 5H) ppm. $^{13}$C-NMR (400 MHz, methanol-d$_4$) δ=170.53, 53.87, 52.61, 33.57, 30.91 ppm. HRMS (ESI$^+$): calc. for C$_{10}$H$_{21}$N$_2$O$_4$S$_2$$^+$ [M+H]$^+$: 297.0864; found: 297.09380. IR (cm$^{-1}$): $\tilde{v}$=3373, 2854, 2611, 2003, 1738, 1591, 1503, 1439, 1224, 1139, 860.

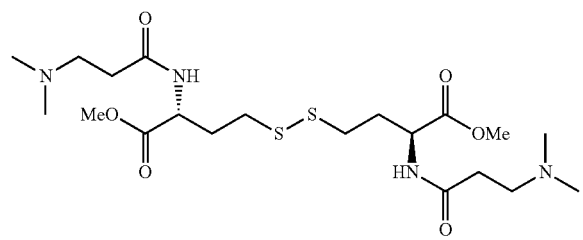

Methyl (2R)-2-[3-(dimethylamino)propanamido]-4-({(3S)-3-[3-(dimethyl-amino) propan amido]-4-methoxy-4-oxobutyl}disulfanyl)butanoate (4) Typical Procedure 2 (TP2)

To a dry and Ar-flushed 50 mL Schlenk-flask, equipped with a stirring bar and a septum, was added the commer-cially available 3-(dimethylamino)propanoic acid hydrochloride (370 mg, 2.40 mmol, 2.4 equiv) and the methyl ester 3 (300 mg, 0.61 mmol, 1.0 equiv) and dissolved in 5 mL anhydrous DMF. Then, TEA (0.29 mL, 2.12 mmol, 3.5 equiv), HOBT (340 mg, 2.50 mmol, 2.5 equiv) and EDC (502 mg, 2.61 mmol, 2.6 equiv) were added and stirred for 2 h at 60° C. The resulting orange slurry reaction mixture was concentrated via vacuo. Purification by flash column chromatography (silica gel, DCM/MeOH 16:1) furnished 4 as a white solid (426 mg, 85%).

$^1$H-NMR (800 MHz, methanol-d$_4$) δ=4.62-4.55 (m, 1H), 3.75 (d, J=1.5, 2H), 3.37 (s, 1H), 2.84-2.79 (m, 1H), 2.78-2.72 (m, 1H), 2.71-2.63 (m, 2H), 2.46 (td, J=7.3, 2.8, 2H), 2.30 (s, 6H), 2.10-2.04 (m, 1H) ppm. $^{13}$C-NMR (201 MHz, methanol-d$_4$) δ=174.37, 173.54, 52.88, 52.37, 49.85, 35.59, 35.52, 34.14, 32.13 ppm. HRMS (ESI$^+$): calc. for C$_{20}$H$_{39}$N$_4$O$_6$S$_2$$^+$ [M+H]$^+$: 494.2233; found: 495.23034. IR (cm$^{-1}$): $\tilde{v}$=3382, 2953, 2833, 2498, 2069, 1733, 1643, 1548, 1439, 1222, 1173, 1119, 977, 856.

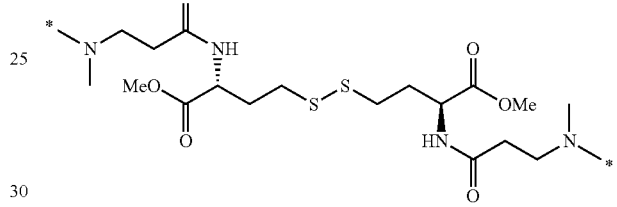

Dimethyl-4,4'-disulfanediyl(2R,2'S)-bis(2-(3-(methyl(methyl-$^{13}$C)amino)-propanamido)-butanoate) (4**)

Following TP2 the previously synthesized 3-{methyl [($^{13}$C)methyl]amino}propanoic acid hydrochloride 10 (220 mg, 1.42 mmol, 2.20 equiv) and methyl ester 3 (238 mg, 0.645 mmol, 1.00 equiv) furnished 4** as a white solid (200 mg, 62%).

$^1$H NMR (CDCl$_3$, 400 MHz): δ 4.57 (ddd, J=8.5, 4.8, 3.1 Hz, 1H), 3.73 (s, 6H), 2.83-2.59 (m, 4H), 2.46-1.99 (m, 20H). HRMS (ESI$^+$): calc. for C$_{18}$$^{13}$C$_2$H$_{39}$N$_4$O$_6$S$_2$$^+$[M+H]$^+$: 497.22889; found: 497.23792.

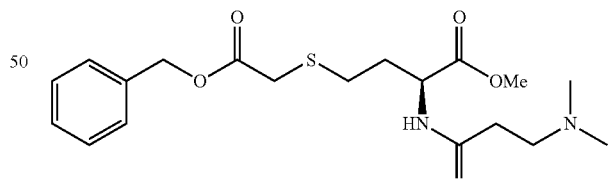

Methyl (2S)-4-{[2-(benzyloxy)-2-oxoethyl]sulfanyl}-2-[3-(dimethylamino)propanamido]butanoate (5) Typical Procedure 3 (TP3)

The previously synthesized disulfide 4 (750 mg, 1.51 mmol, 1.0 equiv) was added to a dry and Ar-flushed 50 mL Schlenk-flask, equipped with a stirring bar and a septum and dissolved in a mixture of 5 mL H$_2$O and 15 mL DMF. Then, NaHCO$_3$ (535 mg, 6.37 mmol, 4.2 equiv) and TCEP (435 mg, 1.51 mmol, 1.0 equiv) was added to the reaction mixture. After completion of the reduction via mass the commercially available benzyl bromoacetate (0.6 mL, 3.79 mmol, 2.50 equiv) was added and stirred for 2 h at rt. The resulting reaction mixture was then concentrated via vacuo and purified by flash column chromatography (silica gel, 5% MeOH in DCM) furnished 5 as a colourless oil (510 mg, 42%).

$^1$H-NMR (400 MHz, methanol-d$_4$) δ=7.53-7.15 (m, 5H), 5.18 (s, 2H), 4.56 (dd, $^3$J=8.9, $^2$J=4.8 Hz, 1H), 3.71 (s, 3H), 3.33 (s, 2H), 2.75-2.58 (m, 4H), 2.45 (t, $^3$J=7.2 Hz, 2H), 2.29 (s, 6H), 2.17-2.05 (m, 1H), 2.02-1.90 (m, 1H) ppm. $^{13}$C-NMR (151 MHz, CDCl$_3$) δ=172.58, 172.51, 170.15, 135.60, 128.73, 128.52, 128.37, 67.18, 55.11, 52.47, 51.05, 44.59, 33.52, 32.82, 31.82, 28.47 ppm. HRMS (ESI$^+$): calc. for C$_{19}$H$_{29}$N$_2$O$_5$S$^+$ [M+H]$^+$: 397.1719; found: 397.17908. IR (cm$^{-1}$): ṽ=3285, 2950, 2864, 1736, 1655, 1539, 1455, 1440, 1374, 1271, 1213, 1170, 1146, 1025, 748, 698.

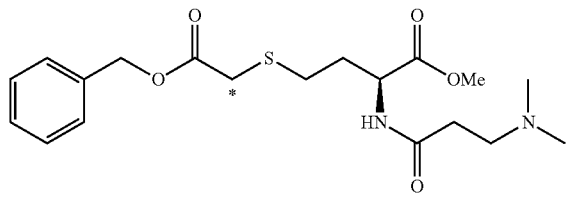 [SMILES: COC(=O)[C@H](CCSCC(=O)OCc1ccccc1)NC(=O)CCN(C)C]

Methyl (2S)-4-{[2-(benzyloxy)-2-oxo(1-$^{13}$C)ethyl]sulfanyl}-2-[3-(dimethylamino)propanamido]butanoate (5*)

Following TP3, the disulfide 4 (370 mg, 0.75 mmol, 1.0 equiv) react with the previously synthesized benzyl bromo (2-$^{13}$C)acetate 11 (294 μL, 1.86 mmol, 2.3 equiv) furnished 5* as a colourless oil (550 mg, 92%).

$^1$H-NMR (400 MHz, methanol-d$_4$) δ=7.42-7.28 (m, 5H), 5.16 (s, 2H), 4.59-4.52 (m, 1H), 3.70 (s, 3H), 3.50 (s, 1H), 3.15 (s, 1H), 2.93 (t, J=7.0 Hz, 2H), 2.75-2.60 (m, 2H), 2.56 (t, J=7.0 Hz, 2H), 2.50 (s, 6H), 2.19-2.05 (m, 1H), 2.04-1.86 (m, 1H) ppm. HRMS (ESI$^+$): calc. for C$_{18}$$^{13}$CH$_{29}$N$_2$O$_5$S$^+$ [M+H]$^+$: 398, 1752; found: 398.18235.

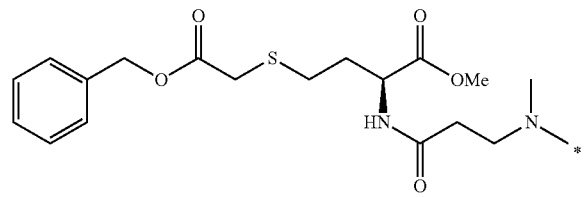 [SMILES: COC(=O)[C@H](CCSCC(=O)OCc1ccccc1)NC(=O)CCN(C)C]

Methyl (2S)-4-{[2-(benzyloxy)-2-oxoethyl]sulfanyl}-2-(3-{methyl[($^{13}$C) methyl]amino}propanamido)butanoate (5**)

Following TP3, the disulfide 4 (200 mg, 0.40 mmol, 1.0 equiv) furnished 5 as a colourless oil (252 mg, 79%).

$^1$H-NMR (400 MHz, methanol-d$_4$): δ=7.40-7.28 (m, 5H), 5.15 (s, 2H), 4.53 (dd, J=8.93, 4.90 Hz), 3.69 (s, 3H), 2.73-2.56 (m, 4H), 2.44-1.87 (m, 10H). $^{13}$C-NMR (101 MHz, methanol-d$_4$) δ=174.49, 173.61, 171.96, 137.34, 129.58, 129.32, 129.25, 67.94, 56.03, 52.80, 52.55, 45.08, 34.17, 33.97, 32.01, 29.51. HRMS (ESI) calc. for C$_{18}$$^{13}$CH$_{29}$N$_2$O$_5$S$^+$ [M+H]$^+$: 398.18252; found: 398.18256.

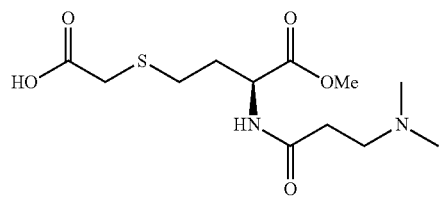 [SMILES: COC(=O)[C@H](CCSCC(=O)O)NC(=O)CCN(C)C]

({(3S)-3-[3-(Dimethylamino)propanamido]-4-methoxy-4-oxobutyl}sulfanyl)acetic acid (6) Typical Procedure 4 (TP4)

The previously synthesized benzyl-protected sulfide 5 (160 mg, 0.40 mmol, 1.0 equiv) was added to a dry and Ar-flushed 25 mL Schlenk-flask, equipped with a stirring bar and a septum and dissolved in 3-4 mL of 10% formic acid-methanol. Then, approximately 160 mg of palladium black catalyst was added to the reaction mixture and stirred for 2 h at 40° C. After completion of the deprotection via mass and TLC the reaction mixture was filtered, concentrated via vacuo and purified by flash column chromatography (silica gel, 25% MeOH in DCM) furnished 6 as a colourless oil (100 mg, 81%).

$^1$H-NMR (400 MHz, methanol-d$_4$) δ=4.61 (dd, J=9.4, 4.2 Hz, 1H), 3.27 (t, J=6.8 Hz, 1H), 3.21 (t, J=6.5 Hz, 1H), 3.12 (s, 2H), 2.75 (s, 6H), 2.73-2.55 (m, 3H), 2.18-2.07 (m, 1H), 2.05-1.93 (m, 1H) ppm. LRMS (ESI$^+$): calc. for C$_{12}$H$_{23}$N$_2$O$_5$S$^+$ [M+H]$^+$: 307, 1249; found: 307.10. IR (cm$^{-1}$): ṽ=3253, 1734, 1652, 1574, 1468, 1372, 1217, 1147, 1084, 977, 761.

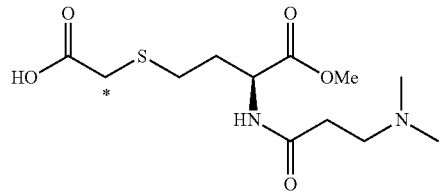 [SMILES: COC(=O)[C@H](CCSCC(=O)O)NC(=O)CCN(C)C]

({(3S)-3-[3-(Dimethylamino)propanamido]-4-methoxy-4-oxobutyl}sulfanyl)(2-$^{13}$C)acetic acid (6*)

Following TP4: 5* (580 mg, 1.46 mmol, 1.0 equiv) furnished 6* as a colourless oil (280 mg, 62%).

$^1$H-NMR (400 MHz, methanol-d$_4$) δ=4.62 (dd, J=4.62 (dd, J=9.4, 4.2, 1H), 3.72 (s, 3H), 3.35 (s, 2H), 3.30-3.24 (m, 2H), 3.17 (dq, J=13.0, 6.4, 1H), 2.74 (s, 6H), 2.72-2.60 (m, 4H), 2.18-1.94 (m, 2H) ppm. $^{13}$C-NMR (101 MHz, methanol-d$_4$) δ=173.85, 172.39, 170.21, 55.22, 52.79, 49.85, 44.01, 37.30, 31.80, 31.62, 29.24 ppm. HRMS (ESI$^+$): calc. for C$_{11}$$^{13}$CH$_{23}$N$_2$O$_5$S$^+$ [M+H]$^+$: 308.1283; found: 308.13564.

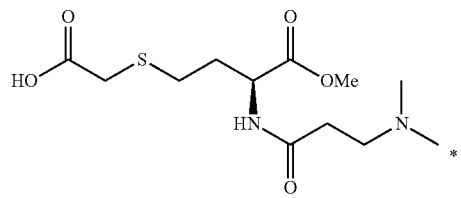 [SMILES: COC(=O)[C@H](CCSCC(=O)O)NC(=O)CCN(C)C]

{[(3S)-4-Methoxy-3-(3-{methyl[($^{13}$C)methyl]amino}propanamido)-4-oxobutyl]sulfanyl}acetic acid (6**)

Following TP4: 5 (252 mg, 0.63 mmol, 1.0 equiv) furnished 6 as a colourless oil (181 mg, 93%).

$^1$H NMR (400 MHz, methanol-d$_4$): δ 4.61 (dd, J=9.5, 4.2 Hz, 1H), 3.70 (s, 3H), 3.38-3.16 (m, 4H), 3.08 (d, J=3.26 Hz, 2H), 2.94-2.59 (s, 10H) ppm. HRMS (ESI$^+$): calc. for C$_{11}$$^{13}$CH$_{23}$N$_2$O$_5$S$^+$ [M+H]$^+$: 308.13557; found 308.13569.

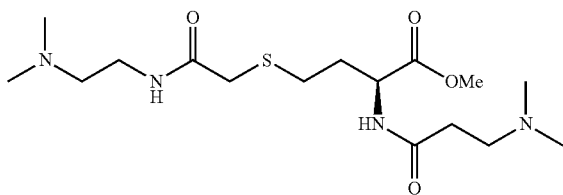

Methyl (2S)-4-[(2-{[2-(dimethylamino)ethyl]amino}-2-oxoethyl)sulfanyl]-2-[3-(dimethylamino)propanamido]butanoate (7): Typical Procedure 5 (TP5)

The previously synthesized acid 6 (100 mg, 0.33 mmol, 1.0 equiv) was added to an dry and Ar-flushed 50 mL Schlenk-flask, equipped with a stirring bar and a septum and dissolved in 10 mL of dry DMF. Then, the commercially available N$^1$,N$^2$-dimethylethane-1,2-diamine (42 µL, 0.39 mmol, 1.2 equiv), DIPEA (83 µL, 0.49 mmol, 1.5 equiv) and PyBOP (203 mg, 0.39 mmol, 1.2 equiv) was added and the reaction mixture was stirred at rt for 1 h. After completion of the amidation via mass the reaction mixture was concentrated via vacuo and purified by flash column chromatography (silica gel, 1:12 MeOH/DCM) furnished 7 as a colourless oil (90 mg, 73%).

$^1$H-NMR (400 MHz, methanol-d$_4$) δ=4.56 (dd, J=9.0, 4.8, 1H), 3.72 (s, 3H), 3.38-3.32 (m, 2H), 3.19 (d, J=1.3, 2H), 2.74-2.57 (m, 4H), 2.47 (dt, J=11.6, 6.8, 4H), 2.30 (d, J=4.3, 12H), 2.12 (dddd, J=13.2, 8.3, 7.2, 4.9, 1H), 2.03-1.92 (m, 1H) ppm. $^{13}$C-NMR (101 MHz, methanol-d$_4$) δ=174.36, 173.65, 172.47, 59.04, 55.99, 52.82, 52.64, 45.47, 45.03, 38.22, 35.97, 34.00, 32.11, 29.70 ppm. LRMS (ESI$^+$): calc. for C$_{16}$H$_{33}$N$_4$O$_4$S$^+$ [M+H]$^+$: 377.2144; found: 377.19. IR (cm$^{-1}$): ṽ=3375, 2878, 17740, 1597, 1509, 1439, 1226, 1144, 1066, 1022, 903, 843, 744.

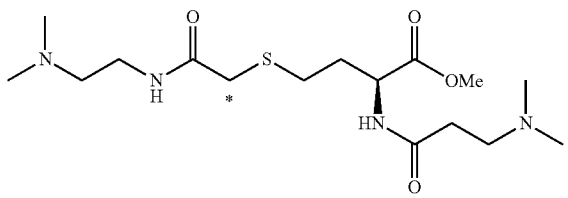

Methyl (2S)-4-{[2-{[2-(dimethylamino)ethyl]amino}-2-oxo(1-$^{13}$C)ethyl]sulfanyl}-2-[3-(dimethylamino)propanamido]butanoate (7*)

Following TP5, 6* (270 mg, 0.87 mmol, 1.0 equiv) furnished 7* as a colourless oil (246 mg, 74%).

$^1$H-NMR (400 MHz, methanol-d$_4$) δ=4.56 (dd, J=9.0, 4.8, 1H), 3.72 (s, 3H), 3.36 (d, J=6.2, 2H), 3.33 (s, 1H), 3.01 (s, 1H), 2.74-2.58 (m, 4H), 2.47 (dt, J=11.4, 7.0, 4H), 2.30 (d, J=4.1, 13H), 2.18-1.92 (m, 3H), 1.29-1.15 (m, 1H) ppm. LRMS (ESI$^+$): calc. for C$_{15}$$^{13}$CH$_{33}$N$_4$O$_4$S$^+$ [M+H]$^+$: 378.2178; found: 378.24.

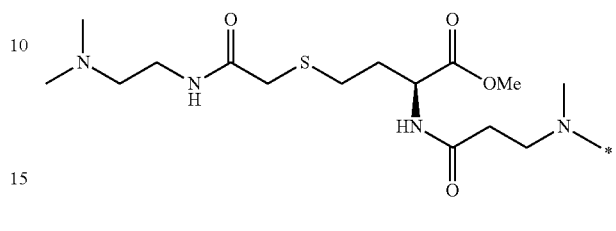

Methyl (2S)-4-[(2-{[2-(dimethylamino)ethyl]amino}-2-oxoethyl)sulfanyl]-2-(3-{methyl[($^{13}$C)methyl]amino}propanamido)butanoate (7**)

Following TP5, 6 (181 mg, 0.59 mmol, 1.0 equiv) furnished 7 as a colourless oil (173 mg, 78%).

$^1$H-NMR (400 MHz, methanol-d$_4$): δ 4.46 (dd, J=9.0, 4.8 Hz, 1H), 3.62 (s, 3H), 3.25 (t, J=6.95 Hz, 2H), 3.09 (s, 2H), 2.66-2.48 (m, 4H), 2.44-1.80 (m, 18H) ppm. $^{13}$C-NMR (101 MHz, methanol-d$_4$): δ 172.94, 172.29, 171.13, 57.62, 54.56, 51.45, 51.26, 44.04, 43.59, 36.81, 34.57, 34.22, 32.49, 30.69, 28.31 ppm. HRMS (ESI$^+$): calc. for C$_{15}$$^{13}$CH$_{33}$N$_4$O$_4$S$^+$ [M+H]$^+$: 378.22506; found 378.22516.

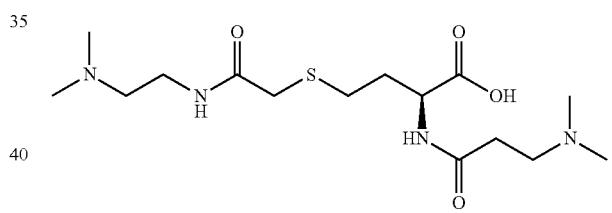

(2S)-4-[(2-{[2-(Dimethylamino)ethyl]amino}-2-oxoethyl)sulfanyl]-2-[3-(dimethylamino)propanamido]butanoic Acid (8)

Typical procedure 6 (TP6): The previously synthesized compound 7 (90 mg, 0.24 mmol, 1.0 equiv) was dissolved in a mixture of 2 mL H$_2$O and 5 mL MeOH. Then LiOH (17 mg, 0.71 mmol, 3.0 equiv) was added and the reaction mixture was stirred at rt for 1 h. After completion of the saponification, the product was desalinated furnished 8 as a white solid (86.6 mg, 100%).

$^1$H-NMR (400 MHz, methanol-d$_4$) δ=4.55 (dd, J=9.3, 4.5, 1H), 3.64 (t, J=5.9, 2H), 3.46 (t, J=6.7, 2H), 3.35 (t, J=6.0, 2H), 2.95 (d, J=13.2, 13H), 2.90-2.83 (m, 2H), 2.81-2.64 (m, 2H), 2.22-2.11 (m, 1H), 2.09-1.97 (m, 1H) ppm. $^{13}$C-NMR (101 MHz, methanol-d$_4$) δ=174.78, 173.70, 171.90, 58.04, 54.90, 52.72, 43.88, 43.72, 43.63, 36.19, 36.00, 32.07, 30.75, 30.10 ppm. HRMS (ESI$^-$): calc. for C$_{15}$H$_{29}$N$_4$O$_4$S$^-$ [M-H]$^-$: 361, 1910; found: 361.19188. IR (cm$^{-1}$): ṽ=3368, 2916, 1743, 1632, 1524, 1439, 1311, 1227, 1160, 1059, 984, 845.

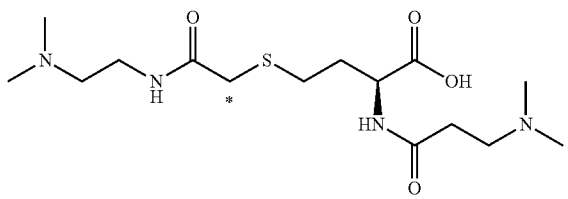

(2S)-4-{[2-{[2-(Dimethylamino)ethyl]amino}-2-oxo (1-¹³C)ethyl]sulfanyl}-2-[3-(dimethylamino)pro-panamido]butanoic Acid (8*)

Following TP6: 7* (220 mg, 0.58 mmol, 1.0 equiv) furnished 8* as a white solid (210 mg, 99%).

¹H-NMR (400 MHz, methanol-$d_4$) δ=4.33 (dd, J=7.8, 4.6, 1H), 3.39-3.32 (m, 3H), 3.02 (s, 1H), 2.67-2.56 (m, 4H), 2.45 (dt, J=14.7, 7.1, 4H), 2.27 (d, J=3.2, 13H), 2.18-1.87 (m, 2H) ppm. ¹³C-NMR (101 MHz, methanol-$d_4$) δ=176.77, 172.29, 172.26, 57.64, 54.84, 54.15, 44.12, 43.73, 36.99, 36.91, 33.25, 32.65, 28.61 ppm. HRMS (ESI⁻): calc. for $C_{14}{}^{13}CH_{29}N_4O_4S^-$ [M−H]⁻: 362.2021; found: 362.19517.

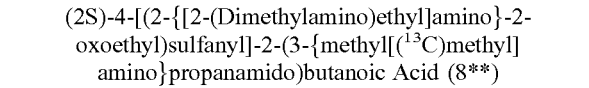

(2S)-4-[(2-{[2-(Dimethylamino)ethyl]amino}-2-oxoethyl)sulfanyl]-2-(3-{methyl[(¹³C)methyl]amino}propanamido)butanoic Acid (8**)

Following TP6: 7 (173 mg, 0.46 mmol, 1.0 equiv) furnished 8 as a white solid (105 mg, 62%).

¹H NMR (400 MHz, methanol-$d_4$): δ 4.33 (dd, J=7.8, 4.6 Hz, 1H), 3.35 (t, J=6.41 Hz, 2H), 3.19 (s, 2H), 2.67-2.56 (m, 4H), 2.50-1.88 (m, 18H). HRMS (ESI⁺): calc. for $C_{14}{}^{13}CH_{31}N_4O_4S^+$ [M+H]⁺: 364.20941; found: 364.20962.

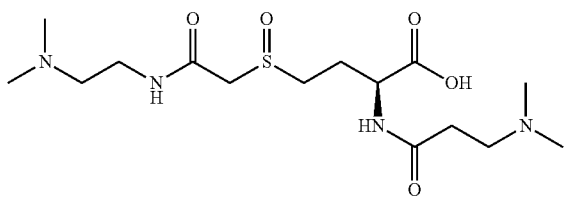

(2S)-4-(2-{[2-(Dimethylamino)ethyl]amino}-2-oxo-ethanesulfinyl)-2-[3-(dimethylamino)propanamido]-butanoic acid (9) Typical Procedure 7 (TP7): 8

(50 mg, 0.14 mmol, 1.0 equiv) was dissolved in 2 mL dest. H₂O. After the pH value was set to pH=2, mCPBA (30.8 mg, 0.14 mmol, 1.0 equiv) was added and the reaction mixture was stirred at rt for 20 min. After completion of the oxidation via mass the resulting reaction mixture was extracted with DCM (4×10 mL) and concentrated via vacuo furnished 9 as a white solid (40 mg, 75%).

¹H-NMR (400 MHz, D₂O) δ=4.46 (td, J=8.1, 5.1, 1H), 3.90 (d, J=14.1, 1H), 3.72 (d, J=14.1, 1H), 3.64-3.51 (m, 2H), 3.34 (td, J=6.7, 1.8, 2H), 3.25 (t, J=6.0, 2H), 3.06-2.85 (m, 2H), 2.82 (d, J=9.5, 13H), 2.76 (t, J=6.8, 2H), 2.34-2.19 (m, 1H), 2.17-2.04 (m, 1H) ppm. ¹³C-NMR (101 MHz, D₂O) δ=174.42, 171.66, 166.86, 56.23, 55.98, 55.88, 53.32, 47.34, 47.19, 42.96, 42.81, 34.87, 29.50, 23.97 ppm. HRMS (ESI⁺): calc. for $C_{15}H_{31}N_4O_5S^+$ [M+H]⁺: 379.1937; found: 379.19624.

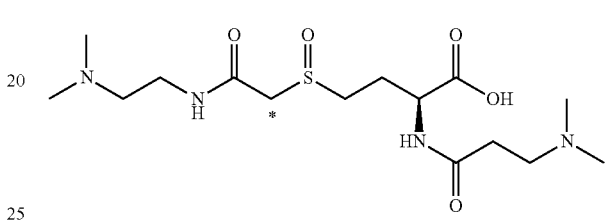

(2S)-4-[2-{[2-(Dimethylamino)ethyl]amino}-2-oxo (1-¹³C)ethanesulfinyl]-2-[3-(dimethylamino)pro-panamido]-butanoic Acid (9*)

Following TP7: 8* (145 mg, 0.39 mmol, 1.0 equiv) furnished 9* as a white solid (150 mg, 99%).

¹H-NMR (400 MHz, D₂O) δ=4.46 (ddt, J=15.6, 10.1, 5.0, 1H), 4.10-3.50 (m, 4H), 3.35 (dt, J=8.0, 4.0, 2H), 3.24 (t, J=6.2, 2H), 3.07-2.95 (m, 2H), 2.82 (d, J=9.4, 13H), 2.75 (q, J=6.7, 3H), 2.60 (s, 1H), 2.29 (dp, J=13.5, 7.4, 1H), 2.19-2.00 (m, 1H) ppm. HRMS (ESI⁺): calc. for $C_{14}{}^{13}CH_{31}N_4O_5S^+$ [M+H]⁺: 380.20432 found: 380.20452.

(2S)-4-(2-{[2-(Dimethylamino)ethyl]amino}-2-oxo-ethanesulfinyl)-2-(3-{methyl[(¹³C)methyl]amino}propanamido)butanoic Acid (9**)

Following TP7: 8 (105 mg, 0.29 mmol, 1.0 equiv) furnished 9 as a white solid (75 mg, 69%).

¹H-NMR (400 MHz, D₂O) δ=4.52 (dd, J=8.7, 5.1 Hz, 1H), 3.71-3.29 (m, 8H), 3.10-2.62 (m, 16H), 2.50-2.17 (m, 2H) ppm. HRMS (ESI⁺): calc. for $C_{14}{}^{13}CH_{31}N_4O_5S^+$[M+H]⁺: 380.20432; found: 380.20424.

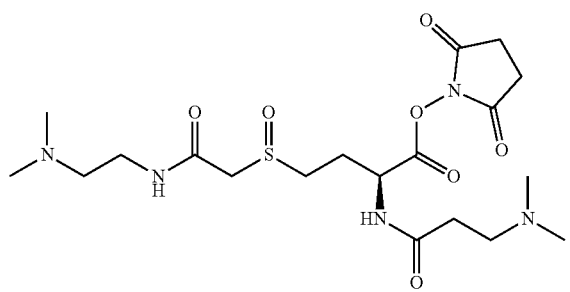

2,5-Dioxopyrrolidin-1-yl (2S)-4-[(2-{[2-(dimethyl-amino)ethyl]amino}-2-oxoethyl)sulfanyl]-2-[3-(dimethylamino)propanamido]butanoate (2) Typical Procedure 8 (TP8)

The previously synthesized sulfoxide 9 (80 mg, 0.22 mmol, 1.0 equiv) was dissolved in 5 mL DMF. Then, dry pyridine (34 µL, 0.42 mmol, 2.0 equiv) and NHS-TFA (89 mg, 0.42 mmol, 2.0 equiv) was added to the reaction mixture. After completion of the ester activation via mass the resulting reaction mixture was concentrated via vacuo. The resulting orange oil was dissolved in acetonitrile and precipitated via acetone furnished 2 as a white solid (35 mg, 35%).

HRMS (ESI$^+$): calc. for $C_{18}{}^{13}CH_{34}N_5O_7S^+$ [M+H]$^+$: 476.2101; found: 476.21727.

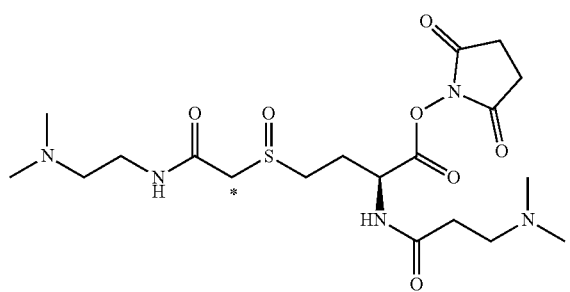

2,5-Dioxopyrrolidin-1-yl (2S)-4-{[2-{[2-(dimethyl-amino)ethyl]amino}-2-oxo(1-$^{13}$C)ethyl]sulfanyl}-2-[3-(dimethylamino)propanamido]butanoate (2*)

Following TP8: 9* (50 mg, 0.13 mmol, 1.0 equiv) furnished 2* as a white solid (20 mg, 32%).

HRMS (ESI$^+$): calc. for $C_{18}{}^{13}CH_{34}N_5O_7S^+$ [M+H]$^+$: 477.2134; found: 477.22124.

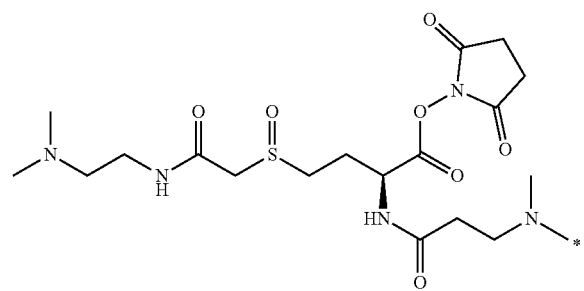

2,5-Dioxopyrrolidin-1-yl (2S)-4-[(2-{[2-(dimethyl-amino)ethyl]amino}-2-oxoethyl)sulfanyl]-2-(3-{methyl[($^{13}$C)methyl]amino}propanamido)butanoate (2**)

Following TP8: 9 (75 mg, 0.20 mmol, 1.0 equiv) furnished 2 as a white solid (30 mg, 31%).

HRMS (ESI$^+$): calc. for $C_{18}{}^{13}CH_{34}N_5O_7S^+$ [M+H]$^+$: 477.2134; found: 477.22064.

The invention claimed is:

1. A reagent for use in mass spectrometry, which is a compound of the general formula (I):

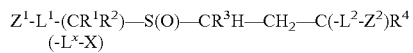

$$Z^1-L^1-(CR^1R^2)-S(O)-CR^3H-CH_2-C(-L^2-Z^2)R^4$$
$$(-L^x-X)$$

wherein

Z$^1$ is charge unit capable of carrying at least one charged moiety

L$^1$ is a bond or a spacer,

Z$^2$ is charge unit capable of carrying at least one charged moiety,

L$^2$ is a bond or a spacer,

R$^1$, R$^2$, R$^3$, R$^4$ are independently hydrogen or C$_1$-C$_3$ alkyl,

X is a reactive group capable of reacting with an analyte molecule, whereby a covalent bond with the analyte molecule is formed, L$^x$ is a bond or spacer.

2. The reagent of claim 1, wherein the charge units Z$^1$ and Z$^2$ comprise each at least one positively charged moiety such as a primary, secondary, tertiary or quaternary ammonium group or a phosphonium group having a pK$_a$ of 10 or higher.

3. The reagent of claim 1, wherein the charge units Z$^1$ and Z$^2$ comprise each at least one negatively charged moiety selected from the group consisting of a phosphate, sulphate, sulphonate or carboxylate group, said moiety having a pK$_b$ of 10 or higher.

4. The reagent of claim 1, wherein the charge units Z$^1$ and Z$^2$ have the same charge.

5. The reagent of claim 1, wherein the charge units Z$^1$ and Z$^2$ are permanently charged.

6. The reagent of claim 1, wherein the reactive group X is
   (i) a carbonyl-reactive group which is capable of reacting with a carbonyl group or a masked carbonyl group on an analyte molecule, wherein the carbonyl-reactive group X is selected from a super-nucleophilic N atom strengthened by an α-effect caused by an adjacent O and/or N atom such as an NH$_2$—N/O, or a dithiol group, or
   (ii) a thiol-reactive group which is capable of reacting with a thiol group, or
   (iii) an amine reactive group which is capable of reacting with an amine of an analyte molecule.

7. The reagent of claim 1, wherein X is selected from
   (i) a hydrazine group wherein R$^1$ is aryl or C$_{1-4}$ alkyl, particularly C$_1$ or C$_2$ alkyl, optionally substituted,
   (ii) a hydrazone group wherein R$^2$ is aryl or C$_{1-4}$ alkyl, optionally substituted,
   (iii) a hydroxylamino group,
   (iv) a dithiol group,
   (v) an electrophilic alkene group, wherein R$^1$, R$^2$ and R$^3$ are independently H, halogen or C$_{1-4}$ alkyl,
   (vi) an active ester group selected from the group consisting of N-hydroxy succinimide (NHS) or sulfo-NHS, a hydroxybenzotriazole (HOBt), a 1-hydroxy-7-azabenzotriazole (HOAt) group or imidoester —CH$_2$—C(=NH$_2{}^+$)—O—CH$_3$.

8. The reagent of claim 1, which is of the general formula (Ia):

$$Z^1\text{-}L^1\text{-}(CR^1R^2)\text{---}S(O)\text{---}CR^3H\text{---}CH_2\text{---}C(\text{-}L^2\text{-}Z^2)R^4\\(\text{-}L^x\text{-}X^1)$$

wherein
$Z^1$ comprises at least one positively charged moiety such as a primary, secondary, tertiary or quaternary ammonium group,
$L^1$ is a spacer, in particular —C(O)—NH—$(CH_2)_n$— with n being an integer from 1 to 10, wherein n is preferably m,
$Z^2$ is equal to $Z^1$,
$L^2$ is a spacer, in particular —NH—C(O)—$(CH_2)_m$— with m being an integer from 2 to 10,
$R^1$, $R^2$, $R^3$, $R^4$ are hydrogen,
$X^1$ an amine reactive group which is capable of reacting with an amine, e.g. an amino group of an analyte molecule such as an peptide,
$L^x$ is a bond or spacer.

9. The reagent of claim 1, which is of the general formula (Ib):

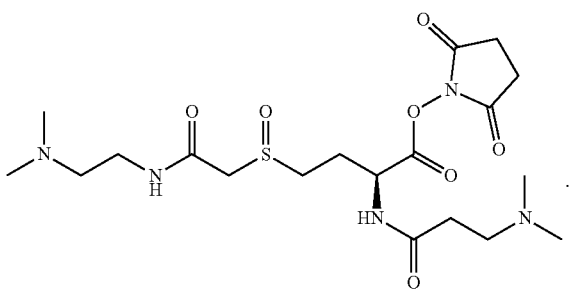

10. A reagent of claim 1, which is an isotopologue.

11. A covalent adduct formed by reaction of the compound of general formula (I) of claim 1 and an analyte molecule.

12. The adduct of claim 11, which is a compound of the general formula (II):

$$Z^1\text{-}L^1\text{-}(CR^1R^2)\text{---}S(O)\text{---}CR^3H\text{---}CH_2\text{---}C(\text{-}L^2\text{-}Z^2)R^4\text{-}\\(L^x\text{-}X')\text{-}T$$

wherein
T is an analyte molecule,
X' is a moiety resulting from the reaction of a group X on the compound (I) with an analyte molecule T,
$Z^1$, $L^1$, $Z^2$, $L^2$, $L^x$, $R^1$, $R^2$, $R^3$ and $R^4$ are as defined in claim 1,
wherein the adduct may carry a permanent positive or negative charge.

13. The adduct of claim 11, wherein the analyte molecule T is an amino group containing peptide.

14. A method for the quantitative mass spectrometric determination of an analyte molecule comprising the steps:
(a) providing at least two analyte samples to be compared,
(b) covalently reacting the analyte molecule in each provided sample with a reagent of general formula (I) according to claim 1, whereby for each sample a different isotopologous reagent of general formula (I) is used and whereby the isotopologues reagents used for different samples are isobaric to each other, and whereby an adduct of the analyte molecule and the reagent in each sample is formed,
(c) combining the at least two samples comprising the adduct of the analyte molecule and the isobaric reagents,
(d) subjecting the combined adducts from step (c) to a mass spectrometric analysis,
wherein the mass spectrometric analysis step (d) preferably comprises:
(i) subjecting ions of the combined isobaric adducts to a first stage of mass spectrometric analysis, whereby the ions of the combined adducts are characterised according to their mass/charge (m/z) ratio,
(ii) causing fragmentation of the combined adduct ions, whereby a reporter ion and a complementary ion having the same charge are yielded from each adduct ion and whereby non-isobaric reporter ions and non-isobaric complementary ions are provided for each originally provided analyte sample to be compared,
(iii) subjecting the non-isobaric reporter ions and non-isobaric complementary ions of step (ii) to a second stage of mass spectrometric analysis,
(iii) relative quantification of the reporter ions of step (ii), and
(iv) relative quantification of the complementary ions of step (ii).

15. The reagent of claim 2, wherein the phosphonium group has a $pK_a$ of 12 or higher.

16. The reagent of claim 10 wherein the isotopologue comprises at least one isotope selected from D, $^{13}$C, $^{15}$N and/or $^{18}$O, in particular $^{13}$C or $^{15}$N.

* * * * *